(12) United States Patent
Balzarini et al.

(10) Patent No.: US 8,193,157 B2
(45) Date of Patent: Jun. 5, 2012

(54) ANTIVIRAL THERAPIES

(75) Inventors: Jan Balzarini, Heverlee (BE); Monika Mazik, Braunschweig (DE)

(73) Assignees: K.U.Leuven Research & Development, Leuven (BE); Technische Universität Carolo Wilhelmina Zu Braunschweig, Braunschweig (DE)

( * ) Notice: Subject to any disclaimer, the term of this patent is extended or adjusted under 35 U.S.C. 154(b) by 924 days.

(21) Appl. No.: 12/067,681

(22) PCT Filed: Sep. 21, 2006

(86) PCT No.: PCT/BE2006/000104
§ 371 (c)(1),
(2), (4) Date: Mar. 21, 2008

(87) PCT Pub. No.: WO2007/033444
PCT Pub. Date: Mar. 29, 2007

(65) Prior Publication Data
US 2009/0042793 A1    Feb. 12, 2009

(30) Foreign Application Priority Data
Sep. 21, 2005    (GB) .................................. 0519169.7

(51) Int. Cl.
*A61K 31/69* (2006.01)
(52) U.S. Cl. .......................................... 514/23; 514/64
(58) Field of Classification Search .................... 514/23, 514/64
See application file for complete search history.

(56) References Cited

U.S. PATENT DOCUMENTS

| | | | |
|---|---|---|---|
| 5,192,788 A | 3/1993 | Dixon et al. | |
| 6,620,805 B1 | 9/2003 | Takle et al. | |
| 6,960,654 B2 * | 11/2005 | Crich et al. | 536/18.5 |

FOREIGN PATENT DOCUMENTS

| | | |
|---|---|---|
| EP | 0173092 | 3/1986 |
| JP | 03/264530 | 11/1991 |
| WO | WO 89/11277 | 11/1989 |
| WO | WO 92/02242 | 2/1992 |
| WO | WO 92/17182 | 10/1992 |
| WO | WO 97/33622 | 9/1997 |
| WO | WO 03/057176 | 7/2003 |
| WO | WO 03/061579 | 7/2003 |
| WO | WO 2005/024416 * | 3/2005 |

OTHER PUBLICATIONS

Goff, PubMed Abstract (J Gene Med 3(6):517-28), Nov.-Dec. 2001.*
Bosseray et al., PubMed Abstract (Pathol Biol (Paris) 50(8):483-92), Oct. 2002.*
Razonable et al., PubMed Abstract (Herpes 10(3):60-5), Dec. 2003.*
Douglas, Jr. Introduction to Viral Diseases, Cecil Textbook of Medicine, 20th Edition, vol. 2, pp. 1739-1747, 1996.*
Mizuochi et al., "HIV Infection and Oligosaccharides: A Novel Approach to Preventing HIV Infection and the Onset of AIDS," *The Journal of Infection and Chemotherapy*, vol. 5, No. 4, pp. 190-195, 1999.
Mizutani et al., "Molecular Recognition of Carbohydrates by Zinc Porphyrins: Lewis Acid/Lewis Base Combinations as a Dominant Factor for Their Selectivity," *Journal of the American Chemical Society*, vol. 119, No. 38, pp. 8991-9001, 1997.
International Search Report and Written Opinion (PCT/BE2006/000104) mailed Oct. 29, 2007.
International Preliminary Report on Patentability (PCT/BE2006/000104) mailed Apr. 3, 2008.
Office Action for Australian Patent Application No. 2006294358, dated May 19, 2011.
Uchimura et al., "Totally Synthetic Polymer with Lectin-Like Function: Induction of Killer Cells by the Copolymer of 3-Acrylamidophenylboronic Acid with N,N-Dimethylacrylamide," *Biotechnol. Bioeng.* 72(3): 307-314 (2001).
Communication for European Patent Application No. 06 790 462.3, dated Jun. 9, 2011.

* cited by examiner

*Primary Examiner* — Deepak Rao
(74) *Attorney, Agent, or Firm* — Clark & Elbing LLP

(57) ABSTRACT

The field of the invention relates to the use of carbohydrate binding compounds as a medicine, their use to treat or prevent viral infections, their use to manufacture a medicine to treat or prevent viral infections and their use in a vaccination strategy. The present invention relates to the use of said compounds to manufacture a medicine to treat or prevent viral infections of subjects, more in particular infections with viruses having glycosilated envelop proteins such as Retroviridae (i.e. Lentivirinae), like HIV (human immunodeficiency virus), Flaviviridae, like HCV (hepatitis C virus), Hepadnaviridae, like HBV (hepatitis B virus), Coronaviridae, like SARS corona virus, and Orthomyxoviridae, like influenza A, B or C.

6 Claims, 6 Drawing Sheets

SEQUENCE LISTING

<160> NUMBER OF SEQ ID NOS: 3

<210> SEQ ID NO 1
<211> LENGTH: 21
<212> TYPE: DNA
<213> ORGANISM: Artificial

```
-continued

<220> FEATURE:
<223> OTHER INFORMATION: primer

<400> SEQUENCE: 1
ccgtctgtgc cttctcatct g                                         21

<210> SEQ ID NO 2
<211> LENGTH: 29
<212> TYPE: DNA
<213> ORGANISM: Artificial
<220> FEATURE:
<223> OTHER INFORMATION: primer

<400> SEQUENCE: 2
agtccaagag tyctcttatr yaagacctt                                 29

<210> SEQ ID NO 3
<211> LENGTH: 26
<212> TYPE: DNA
<213> ORGANISM: Artificial
<220> FEATURE:
<223> OTHER INFORMATION: probe

<400> SEQUENCE: 3
ccgtgtgcac ttcgcttcac ctctgc                                    26
```

ANTIVIRAL THERAPIES

CROSS-REFERENCE TO RELATED APPLICATIONS

Figure 1:
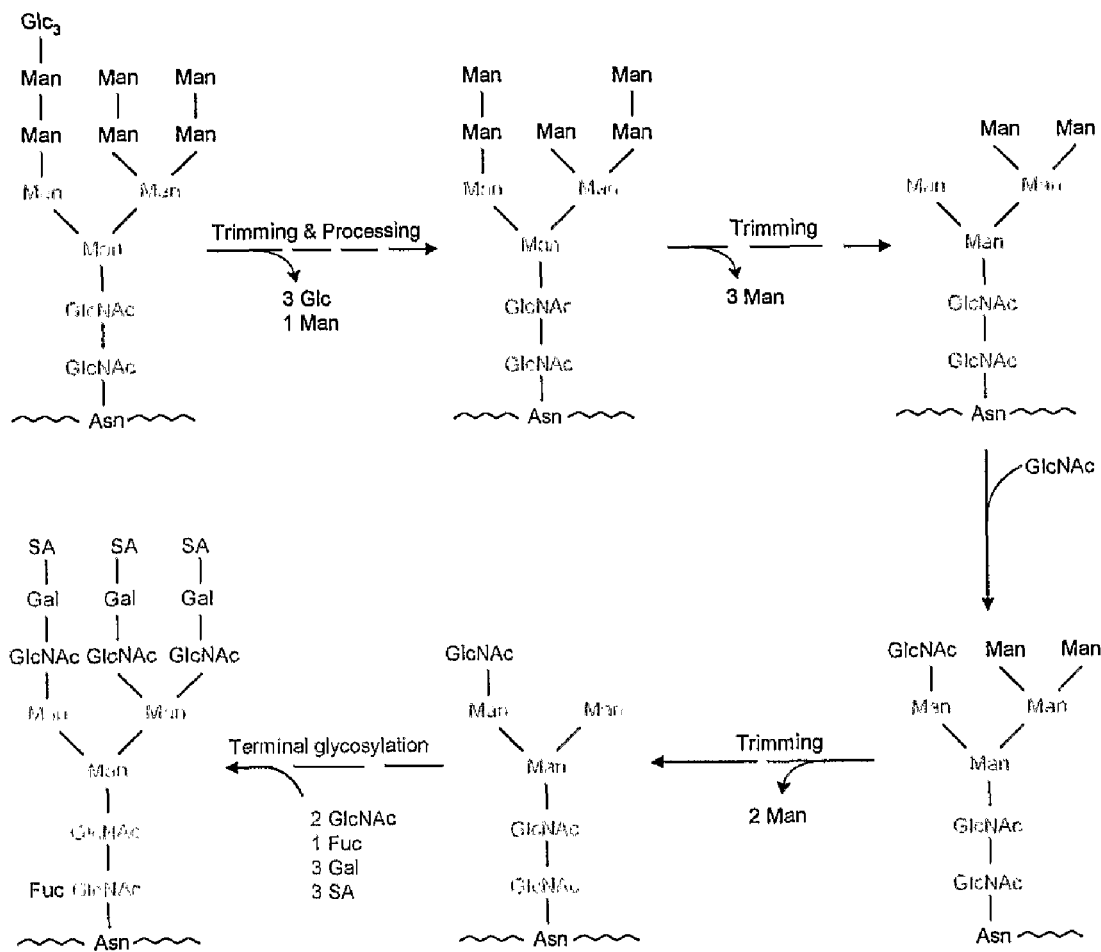

This application is the U.S. National Stage of International Application No. PCT/BE2006/000104, filed Sep. 21, 2006, which claims the benefit of British Patent Application No. 0519169.7, filed Sep. 21, 2005.

FIELD OF THE INVENTION

The field of the invention relates to the use of carbohydrate binding compounds as a medicine, their use to treat or prevent viral infections, their use to manufacture a medicament to treat or prevent viral infections and their use in a vaccination strategy. The present invention relates to the use of said compounds to manufacture a medicine to treat or prevent viral infections of subjects, more in particular infections with viruses having glycosilated envelop proteins such as Retroviridae (i.e. Lentivirinae), like HIV (human immunodeficiency virus), Flaviviridae like, HCV (hepatitis C virus), Hepadnaviridae, like HBV (hepatitis B virus), Coronaviridae, like SARS-CoV, and Orthomyxoviridae, like influenza virus A, B and C.

BACKGROUND OF THE INVENTION

Viral infections remain a major medical problem worldwide because of a lack of efficient therapy, prevention or vaccination strategy and because of the rapid development of resistance. Many virusses and virus families causing problematic disorders can be identified. The family of the Flaviviridae (i.e. Dengue virus, HCV, Yellow Fever virus, West Nile virus) can cause major health problems worldwide for mammals including humans. The family of the Herpesviridae includes important human pathogens like Herpes simplex virus (HSV) type 1 and 2 and cause disorders like Herpes Labialis and Herpes Genitalis and so on. Coronaviridae now approximately comprises 15 species, causing in humans respiratory infections (including Severe Acute Respiratory Syndrome (SARS), enteric infections and rarely neurological syndromes).

The World Health Organization estimates that world-wide 170 million people (3% of the world's population) are chronically infected with HCV. These chronic carriers are at risk of developing cirrhosis and/or liver cancer. The only treatment option available today is the use of interferon $\alpha$-2 (or its pegylated from) either alone or combined with ribavirin. However, sustained response is only observed in about 40% of the patients and treatment is associated with serious adverse effects. There is thus an urgent need for potent and selective inhibitors of the replication of the HCV in order to treat infections with HCV. Also outbreaks of Orthomyxoviruses like Influeanza, where no treatment exists, create nowadays regularly commotion on a world-wide basis.

HIV (human immunodeficiency virus) is one of the most problematic viral infections with an estimated 40 million people infected worldwide. Currently available drugs for the treatment of HIV include nucleoside reverse transcriptase (RT) inhibitors (i.e. zidovudine, didanosine, stavudine, lamivudine, zalcitabine, abacavir and emtricitabine), the nucleotide RT inhibitor tenofovir, non-nucleoside reverse transcriptase inhibitors (i.e. nevirapine, delavirdine and efavirenz), peptidomimetic protease inhibitors (i.e. saquinavir, indinavir, ritonavir, nelfinavir, amprenavir and lopinavir) and the entry inhibitor enfuvirtide. These compounds are mostly used in combination therapies (HAART) wherein different classes of anti-HIV compounds are combined.

Entry inhibitors are a relatively new class of anti-HIV compounds and the process of HIV entry into host cells provides different targets for the development of antiretroviral drugs. Every step of HIV entry can theoretically be inhibited, namely 1. binding of HIV to the CD4 receptor, 2. binding to coreceptors and 3. fusion of virus and cell.

The envelope protein of HIV is a trimer, with each of the components consisting of 2 subunits, gp41 and gp120. The gp120 subunit of the viral envelope binds to the cellular CD4 molecule; this receptor binding induces conformational changes in the viral envelope protein that include exposure of a previously hidden, highly conserved domain that binds to a second receptor (coreceptor). The viral coreceptors, CCR5 and CXCR4, are members of the chemokine subfamily of 7-transmembrane domain receptors. Coreceptor binding induces conformational changes in the gp41 subunit that result in the insertion of a fusion peptide into the cell membrane and the binding of gp41 helical region 1 and helical region 2, which mechanically draws the viral and cell membranes together and permits membrane fusion.

Enfuvirtide, a fusion inhibitor, is the only entry inhibitor currently approved by the US Food and Drug Administration for use as an antiretroviral agent. Basically, enfuvirtide mimics the structure of helical region 2 of gp41, which binds with helical region 1. By binding with helical region 1, the drug molecule prevents binding to helical region 2 and thus prevents fusion of the viral and cellular membranes. Other not yet marketed HIV-inhibiting entry inhibitors are known in the art and they interact on different levels of the entry process. These include neutralizing monoclonal antibodies directed against the native trimeric structure of the viral envelope; CD4 binding inhibitors, including BMS-806 (which binds in a cleft of gp120 and thus prevents CD4 binding); CCR5 binding inhibitors and CXCR4 binding inhibitors (e.g., AMD3100); and fusion inhibitors (e.g., the enfuvirtide derivative, T1249).

There exists a variety of carbohydrate-recognizing plant proteins (agglutinins-lectins) that are endowed with anti-HIV activity. The vast majority of carbohydrate-binding plant proteins that show anti-HIV activity are endowed with specificity for $\alpha$(1-3)- and $\alpha$(1-6)-mannose (Man) oligomer binding (21-24). Mannose-binding proteins have also been isolated and characterized from prokaryotic organisms such as cyanovirin from the green-blue algae Nostoc ellipsosporum (25,26) and scytovirin from the cyanobacterium *Scytonema varium* (27). A striking exception among the anti-HIV carbohydrate-binding plant proteins having a different sugar specificity than mannose is represented by UDA, a plant protein derived from the stinging nettle *Urtica dioica* (22). This plant lectin shows specificity for N-acetylglucosamine (GlcNAc) (28,29). These agents have been shown to inhibit the entry process of the virus, in particular fusion (21). They do not only inhibit HIV infection but also prevent HIV transmission by efficiently blocking cell-to-cell contact. Therefore, the sugar-binding proteins have been suggested as potential microbicide drugs (30), and for the mannose-specific cyanovirin, efficacy to prevent virus infection in Rhesus monkeys has been demonstrated, providing proof of concept (31). It is thought that the carbohydrate-binding plant proteins exert their antiviral action by strongly binding to the sugar moieties present at gp120 of HIV, thereby compromising the required conformational changes in gp120/gp41 for optimal interaction with the (co)-receptors and fusion with the target cell membrane.

Also glycopeptide antibiotics have been described as having an anti-HIV activity and potentially interfering with the entry process of HIV.

One of the major hurdles in HIV therapy is the development of drug resistance that heavily compromises the long-term efficacy of the current (combination) medication.

Also, vaccine development faces huge problems, due to the fact that the immune system fails to efficiently control HIV infection. Antibodies against HIV produced by the humoral immune system act against free virus but may also act against virus-infected cells (1). They bind to the envelope protein gp120 present at the surface of HIV. By doing this, they can directly block virus infection (neutralisation) or may trigger effector systems that lead to viral clearance. The antiviral activity can be mediated by both neutralising and non-neutralising antibodies. Whereas the neutralising antibodies (Nabs) bind to viral proteins that are expressed on the envelope of the free virus particles, non-neutralising antibodies bind to viral proteins mainly expressed on virus-infected cells but not significantly expressed on free virus particles. Generally, neutralising antibodies produced by the humoral immunity are crucial for vaccine-mediated protection against viral diseases. They may act by decreasing the viral efficiency of infection, which is then resolved by the cellular immunity. In fact, neutralisation occurs when a fairly large proportion of available sites on the virion are occupied by antibody, which leads to inhibition of virus attachment to host cells or to interference with the viral entry (fusion) process (1).

However, with the envelope glycoprotein gp120 of HIV being the target of virus-neutralising antibodies, it does not elicit efficient neutralising response in infected people (2). First, little of the envelope surface of primary viruses appears accessible for antibody binding, probably because of oligomerisation of the gp120 proteins and the high degree of glycosylation of the proteins (low antigenicity). Second, the mature carbohydrate oligomers constituting the envelope spikes of HIV appears to stimulate only weak antibody responses (low immunogenicity). Third, intensive viral variation compromises an efficient neutralisation by the immune system (high mutational rate). It was recently shown by Wei et al. (3) that the glycan shield on HIV-1 gp120 (approximately 50% of the gp120 molecule exists of glycans) is evolving during the course of HIV infection in the face of a continuously changing antibody repertoire. Indeed, successive populations of escape virus in patients with acute HIV infection contained mutations in the envelope gene that were unexpectedly sparse and involved primarily changes in N-linked glycosylation sites. These continuous changes in glycan packing efficiently prevent neutralising antibody binding but not receptor binding. In the light of these observations, it could be hypothesized that the abundant glycosylation sites at the surface of the gp120 glycoprotein serve to protect against humoral immune response against gp120 epitopes critical for HIV infectivity and/or transmission (4). Indeed, carbohydrate regions of glycoproteins are considered as poor immunogens for several reasons. (i) Carbohydrate moieties exhibit microheterogeneity. A same protein sequence exhibits a broad range of glycoforms, causing the deletion of any single antigenic response (5). (ii) Large carbohydrates are flexible and extend considerably from the protein core, being able to cover potential highly immunogenic epitopes (6). (iii) Viruses fully depend on the host glycosylation machinery, and therefore, the glycans attached to viral proteins (potential antigens) are quite similar to those attached to host glycoproteins, resulting in a better tolerance of these carbohydrates (7).

Thus, host immunity responses are not very efficient mainly due to the low antigenicity and immunogenicity of the HIV envelope gp120, and the capacity of the virus to efficiently hide highly immunogenic epitopes of its envelope by its glycans. However, strong evidence is available that mutant HIV strains that contain deletions in glycosylation sites of their env trigger the production of specific neutralizing antibodies to previously hidden gp120 epitopes.

As a conclusion, for many pathogenic viral infections and specifically enveloped viruses like HIV, HCV or Influenza no efficient treatment is currently available and moreover, the available anti-viral therapies or preventive measures are not sufficient in order to be able to cure, prevent or ameliorate the respective viral infections due to many reasons, like the occurence of resistance and unfavorable pharmacokinetic or safety profiles. Therefore, there is still a stringent need in the art for potent inhibitors of viruses, more specifically enveloped viruses such as HIV, HCV or Influenza. It is the goal of the present invention to satisfy this urgent need by identifying efficient and less harmful treatment or vaccination regimens and pharmaceutically active ingredients and combination of ingredients for the treatment of viral infections in mammals and in humans.

SUMMARY OF THE INVENTION

The present invention provides novel compounds, namely "carbohydrate binding small molecules" with anti-viral activity, more specifically against virusses having glycosilated envelop proteins, more in particular virusses of the family of the Retroviridae, Hepadnaviridae, Coronaviridae, Orthomyxoviridae or Flaviviridae. The present invention furthermore relates to the use of these carbohydrate binding small molecules as a medicine and more specifically to use the compounds as an anti-viral agent and or as part of vaccinations or vaccination strategy. The present invention provides for the use of carbohydrate binding small molecules for the manufacture of a medicament, more in particular for the treatment or prevention of a viral infection, more in particular of an infection with enveloped viruses like HIV, HCV or Influenza. The present invention furthermore provides a combination therapy of "carbohydate binding agents" with other anti-viral agents such as other entry-inhibitors or with inhibitors of the cellular glycosylation enzymes.

In a particular embodiment, the present invention provides for the use of mannose binding small molecules or agents, more in particular α-1,3- and α-1,6-mannose binding small molecules for the manufacture of a medicament for the prevention or treatment of a viral infection in a mammal.

The viral infections referred to for the present invention are enveloped viruses, meaning viruses having glycosilated envelop proteins. The group of enveloped viruses comprises:

- Retroviridae (i.e. Lentivirinae), like HIV (human immunodeficiency virus);
- Flaviviridae, which comprises (i) the Flaviviruses like Yellow fever virus (YFV) and Dengue virus, the Hepaciviruses like HCV (hepatitis C virus) and (iii) the Pestiviruses like Bovine viral diarrhea virus (BVDV);
- Herpesviridae, like Herpes simplex virus type 1 (HSV-1) or type 2 (HSV-2), Varicella-zoster virus (VZV), Cytomegalovirus (CMV) or Human Herpes virus type 6 (HHV-6);
- Poxyiridae, like Vaccinia;
- Hepadnaviridae, like HBV (hepatitis B virus);
- Coronaviridae, like SARS-CoV;
- Orthomyxoviridae, like influenza virus A, B and C;
- Togaviridae;
- Arenaviridae, like Arenavirus;
- Bunyaviridae, like Punta Toro;

Paramyxoviridae, like Respiratory syncytial virus (RSV) or Parainfluenza-3 virus; and Rhabdoviridae.

In a particular embodiment, the group of enveloped viruses consists of viruses with mannose containing envelop glycoproteins, more in particular α-1,3- and α-1,6-mannose containing.

In particular embodiments of the present invention, any virus family or specific virus species can be excluded from treatment or prevention with specific carbohydrate small molecules or agents described herein or mannose binding small molecules or agents described herein.

The present invention also provides for the use of carbohydrate binding agents in a vaccination strategy comprising the use of carbohydrate binding agents as an adjuvans for vaccination strategies. The vaccination strategy may furthermore comprise a glycosilated envelop protein of an enveloped virus such as gp120 for HIV, which is able to induce an immune response, more in particular mutated envelop proteins with accessible epitopes.

The invention also relates to methods for preparation of all such carbohydrate binding small molecules or agents and pharmaceutical compositions comprising them. The present invention also relates to a method of treatment of viral infections, more specifically of infections with enveloped viruses, by using said carbohydrate binding small molecules or agents. The invention also provides for a method of treating or preventing an infection with an enveloped virus in mammals or humans by using said carbohydrate binding molecules and agents, in a particular embodiment by inducing resistance mutations in the envelope to carbohydrate binding small molecules or agents.

The invention thus relates to the use of envelop-carbohydrate binding small molecules, more specifically selected from the group of:

(a) porphyrins and derivatives or analogues thereof as described in Mizutani et al. (J. Am. Chem. Soc. 1997, 119: 8991-9001), more in particular phthalocyanines and derivatives thereof (b) phenylboronic acids comprising compounds or polymers, such as described in Uchimura et al. (Biotechnol. Bioengineer. 2001, 72: 307-314);

(c) Diethylenetriaminecopper(II) complexes, such as in Striegler (Tetrahedron 2001, 57: 2349-2354);

(d) Acyclic pyridine/pyrimidine-based carbohydrate receptors, such as in Mazik et al. (J. Am. Chem. Soc. 2005, 127: 9045-9052);

(e) Multivalent polyphenolic derivatives, such as in Hamashin et at. (Bioorg. Med. Chem. 2003, 11: 4991-4997);

as antiviral compounds, more particularly as compounds active against enveloped viruses such as HIV, HCV and Influenza. The invention also relates to the use of said compounds for the manufacture of a medicine or as a pharmaceutically active ingredient, especially as a virus infection or replication inhibitor, preferably an enveloped virus infection or replication inhibitor, for instance for the manufacture of a medicament or pharmaceutical composition having antiviral activity for the prevention and/or treatment of viral, preferably enveloped viral infections in humans and mammals. The present invention further relates to a method of prevention or treatment of a viral infection, preferably an infection with an enveloped virus in a mammal, including a human, comprising administering to the mammal in need of such treatment a therapeutically effective amount of carbohydrate binding small molecules or agents as an active ingredient, preferably in a mixture with at least a pharmaceutically acceptable carrier.

The invention also relates to pharmaceutical compositions comprising the compounds as described herein in admixture with at least a pharmaceutically acceptable carrier, the active ingredient preferably being in a concentration range of about 0.1 to 100% by weight, and to the use of these derivatives namely as drugs useful for the treatment of subjects suffering from an infection with an enveloped virus.

The invention further relates to the use of a composition comprising (a) one or more carbohydrate binding small molecules as described herein, and (b) one or more viral inhibitors as biologically active agents in respective proportions such as to provide a synergistic effect against a viral infection, preferably a lentiviral infection and more preferably a retroviral infection in a mammal, for instance in the form of a combined preparation for simultaneous, separate or sequential use in retroviral infection therapy. Within the framework of this embodiment of the invention, the retroviral enzyme inhibitors used as a therapeutically active ingredients (b) may belong to categories already known in the art and include, among others, HIV integrase inhibitors such as are known in the art;

Nucleoside, non-nucleoside and nucleotide reverse transcriptase inhibitors such as for instance, dideoxyadenosine, stavudine, zalcitabine, zidovudine, lamivudine, didanosine, nevirapine, delavirdine, efavirenz, tenofovir, foscarnet sodium and the like, HIV protease inhibitors such as for instance saquinavir, ritonavir, indinavir, nelfinavir, amprenavir and the like, HIV fusion inhibitors such as enfevurtide.

Any of the uses mentioned with respect to the present invention may be restricted to a non-medical use, a non-therapeutic use, a non-diagnostic use, or exclusively an in vitro use, or a use related to cells remote from an animal.

In a particular embodiment, the present invention relates to the use of carbohydrate binding small molecules selected from:

(a) phthalocyanines and derivatives thereof;

(b) phenylboronic acids comprising compounds or polymers;

(c) Diethylenetriaminecopper(II) complexes;

(d) Acyclic pyridinelpyrimidine-based carbohydrate receptors; or (e) Multivalent polyphenolic derivatives;

for the manufacture of a medicament for the prevention or treatment of a viral infection of a mammal, more in particular an infection of a mammal with an enveloped virus. In another particular embodiment, the present invention provides for methods of treatment of infections with enveloped viruses comprising the use of the carbohydrate binding small molecules selected from (a) phthalocyanines and derivatives thereof; (b) phenylboronic acids comprising compounds or polymers; (c) Diethylenetriaminecopper(II) complexes; (d) Acyclic pyridine/pyrimidine-based carbohydrate receptors; or (e) Multivalent polyphenolic derivatives. The present invention also relates to pharmaceutical composition comprising the carbohydrate binding small molecules selected from (a) phthalocyanines and derivatives thereof; (b) phenylboronic acids comprising compounds or polymers; (c) Diethylenetriaminecopper(II) complexes; (d) Acyclic pyridine/pyrimidine-based carbohydrate receptors; or (e) Multivalent polyphenolic derivatives.

Another particular embodiment of the present invention relates to the use of the carbohydrate binding agents selected from the lectins like GNA, HHA, CA and UDA for the manufacture of a medicament for the prevention or treatment of infections of mammals with viruses of the Hepadnaviridae, like HBV (hepatitis B virus); the Coronaviridae, like SARS-CoV; the Herpesviridae; the Paramyxoviridae; the Orthomyxoviridae, like influenza virus A, B and C; the Flaviviruses or the Pestiviruses. In another particular embodiment, the present invention provides for methods of treatment of infections with envelop viruses selected from Hepadnaviridae, like HBV (hepatitis B virus); the Coronaviridae, like SARS-CoV; the Herpesviridae; the Paramyxoviridae; the Orthomyxoviridae, like influenza virus A, B and C; the Flaviviruses or the Pestiviruses, comprising the use of the carbohydrate binding agents selected from the lectines.

Another particular embodiment of the present invention relates to the use of the carbohydrate binding small molecules selected from porphyrins for the manufacture of a medicament for the prevention or treatment of infections of mammals with viruses of the Hepadnaviridae, like HBV (hepatitis B virus); the Coronaviridae, like SARS-CoV; the Herpesviridae; the Paramyxoviridae; the Orthomyxoviridae, like influenza virus A, B and C or the Flaviviridae such as HCV. In another particular embodiment, the present invention provides for methods of treatment of infections with envelop viruses selected from Hepadnaviridae, like HBV (hepatitis B virus); the Coronaviridae, like SARS-CoV; the Herpesviridae; the Paramyxoviridae; the Orthomyxoviridae, like influenza virus A, B and C or the Flaviviridae like HCV, comprising the use of porphyrins and derivatives thereof.

Another particular embodiment of the present invention relates to the use of the carbohydrate binding small molecules selected from pradimicin and derivatives thereof for the manufacture of a medicament for the prevention or treatment of infections of mammals with viruses of the Hepadnaviridae, like HBV (hepatitis B virus); the Coronaviridae, like SARS-CoV; the Herpesviridae; the Paramyxoviridae; or the Flaviviridae such as HCV. In another particular embodiment, the present invention provides for methods of treatment of infections with envelop viruses selected from Hepadnaviridae, like HBV (hepatitis B virus); the Coronaviridae, like SARS-CoV; the Herpesviridae; the Paramyxoviridae; or the Flaviviridae like HCV, comprising the use of pradimicin and derivatives thereof.

DETAILED DESCRIPTION OF THE FIGURES

FIG. 1. Biosynthesis of N-linked core oligosaccharides—Generation of glycosylated proteins: The addition of carbohydrates to a dolicholphosphate carrier starts at the cytosolic surface of the endoplasmatic reticulum (ER) membrane and continues at the luminal side of the ER membrane until the core oligosaccharide consisting of two N-acetylglucosamine (GlcNAc), nine mannose (Man) and three glucose (Glc) residues ($GlcNAc_2Man_9Glc_3$) is completed and transferred to asparagine residues of a nascent growing polypeptide chain through the 1-position of GlcNAc (FIG. 1). The 3 terminal glucoses are then trimmed-off by glucosidase I and II, and the terminal ($\alpha$-1,2) mannoses by ER mannosidases. After movement to the Golgi complex, further $\alpha$-1,3- and $\alpha$-1,6-mannose trimming occurs. Addition of one GlcNAc residue is then followed by trimming of 2 Man residues. During subsequent terminal glycosylation, new terminal sugars such as GlcNAc, fucose (Fuc), galactose (Gal) and/or sialic acid (SA) can be added. Only one of the many possible terminal glycosylation pathways is shown in FIG. 1, and the number of branches generated is variable resulting in Golgi complex-generated highly diverse and widely different oligosaccharides present on the peptide asparagine, that is part of a glycosylation NXS/T motif (19). It is clear that all glycans in glycoproteins have a conserved pentasaccharide core exclusively containing 2 GlcNAc and 3 Man units ($GlcNAc_2Man_3$). The other carbohydrates that are built on the two end-standing mannoses of this pentasaccharide core can widely vary depending on the type of protein, cell and species. HIV gp120, however, consists of an unusual high amount of mannoses in its glycans, in particular $\alpha$-1,2 mannose oligomers at the surface of the glycan and $\alpha$-1,3- and $\alpha$-1,6-mannose oligomers between the $\alpha$-1,2-mannose oligomer surface and the $(GlcNAc)_2$ linked to the protein (20).

Abbreviations are: Man, mannose; GlcNAc, N-acetylglucosamine; Glc, glucose; Gal, galactose; SA, sialic acid; Fuc, fucose; Asn, asparagine.

Figure 2:
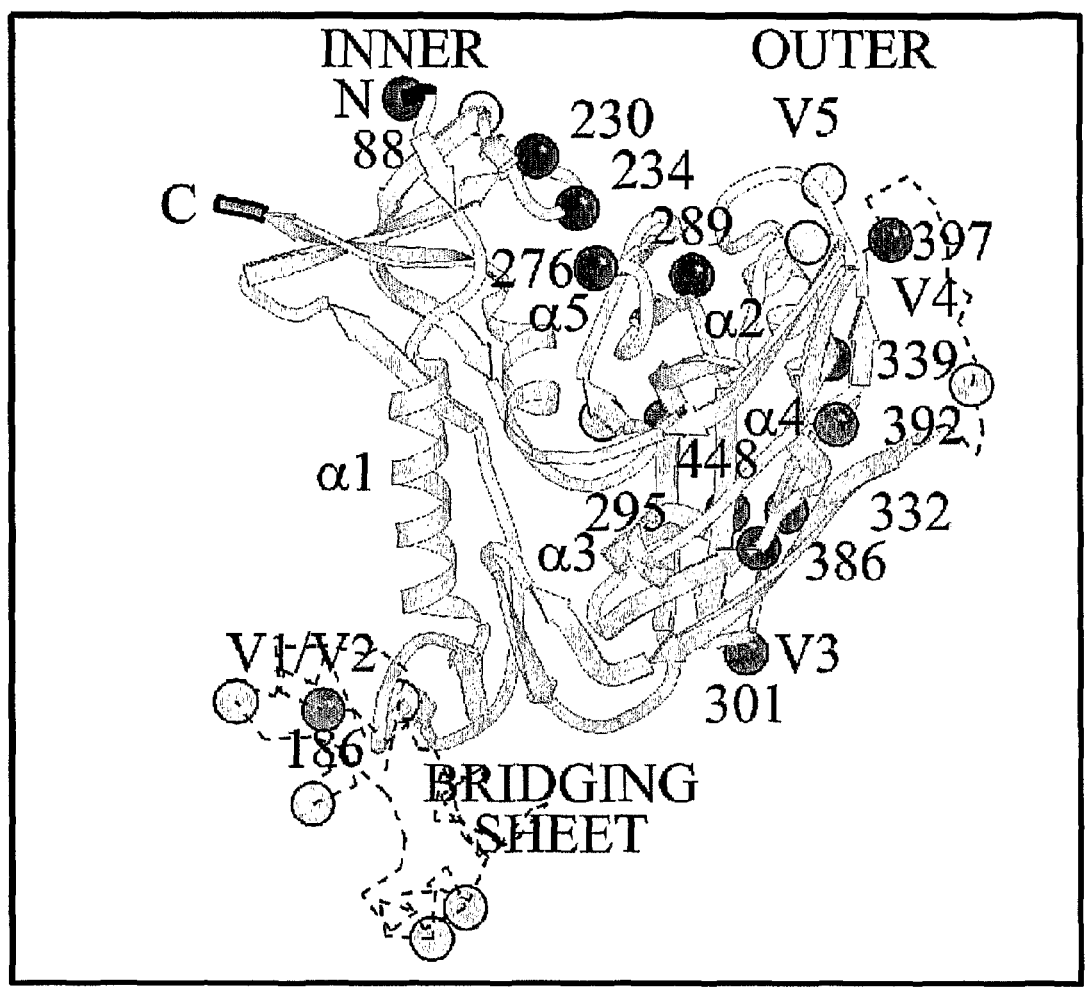

FIG. 2. Glycosylation sites present in HIV-1($III_B$) gp120 are indicated as balls. Those glycosylation sites that were reported to be deleted upon selection of HIV-1 in the presence of mannose-binding agents (GNA, HHA and CV-N) (33,34) are coloured in red. The gp120 structure is according to Kwong et al. (37) and the glycosylation sites are according to Leonard et al. (20). Two areas on the V1/V2 and V4 parts of gp120 are not resolved in the crystal structure. The dashed lines are a modeled representation of these protein parts. (Courtesy of Dr. M. Froeyen, Rega Institute, Leuven, Belgium)

Figure 3:
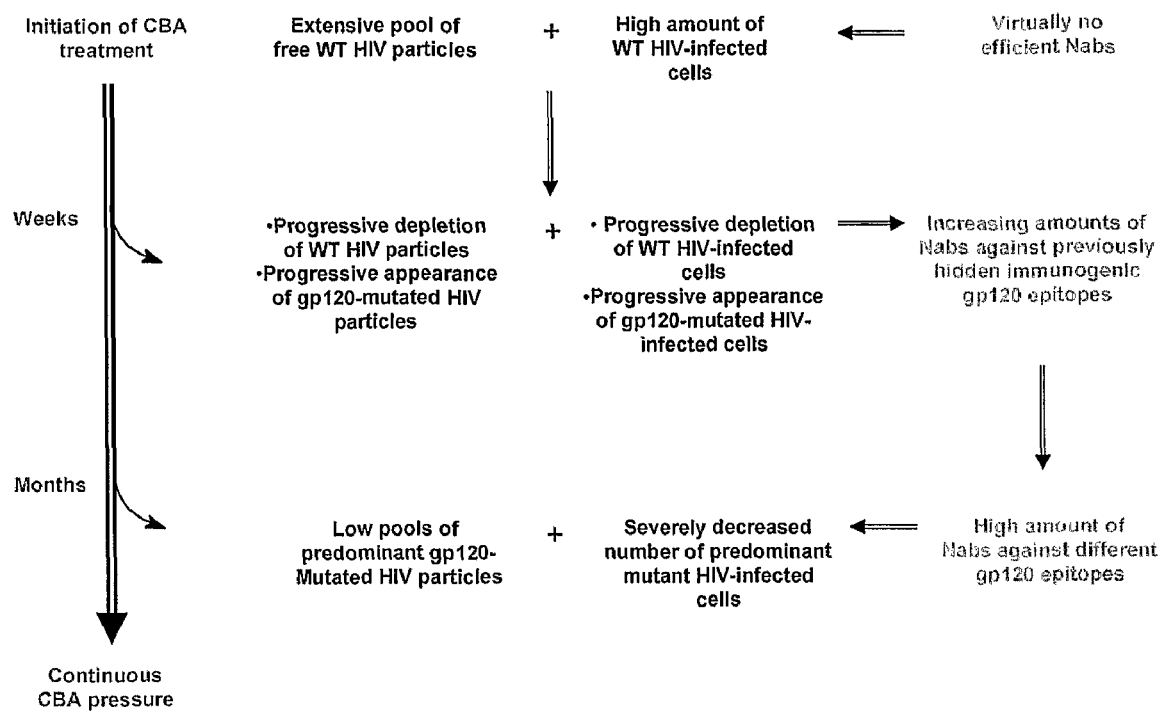

FIG. 3. Schematic overview of the anti-viral carbohydrate binding agents (CBA) concept.

Figure 4:
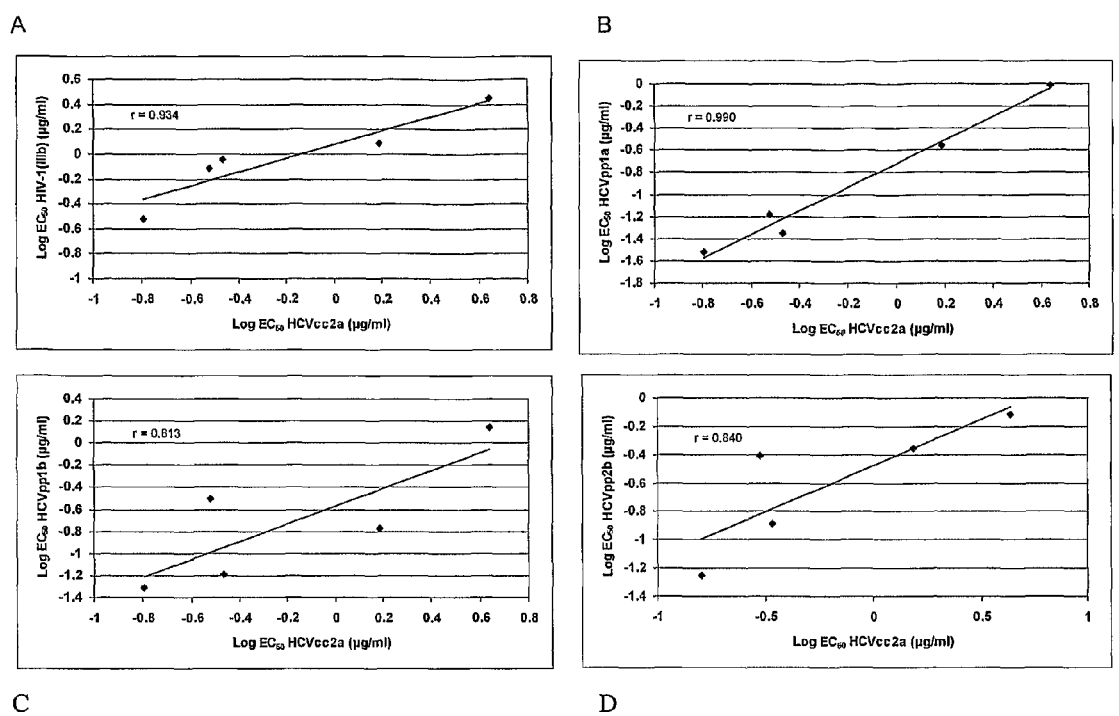

FIG. 4: Correlation between the inhibitory activity of the different CBA against HIV and HCV.

Figure 5:
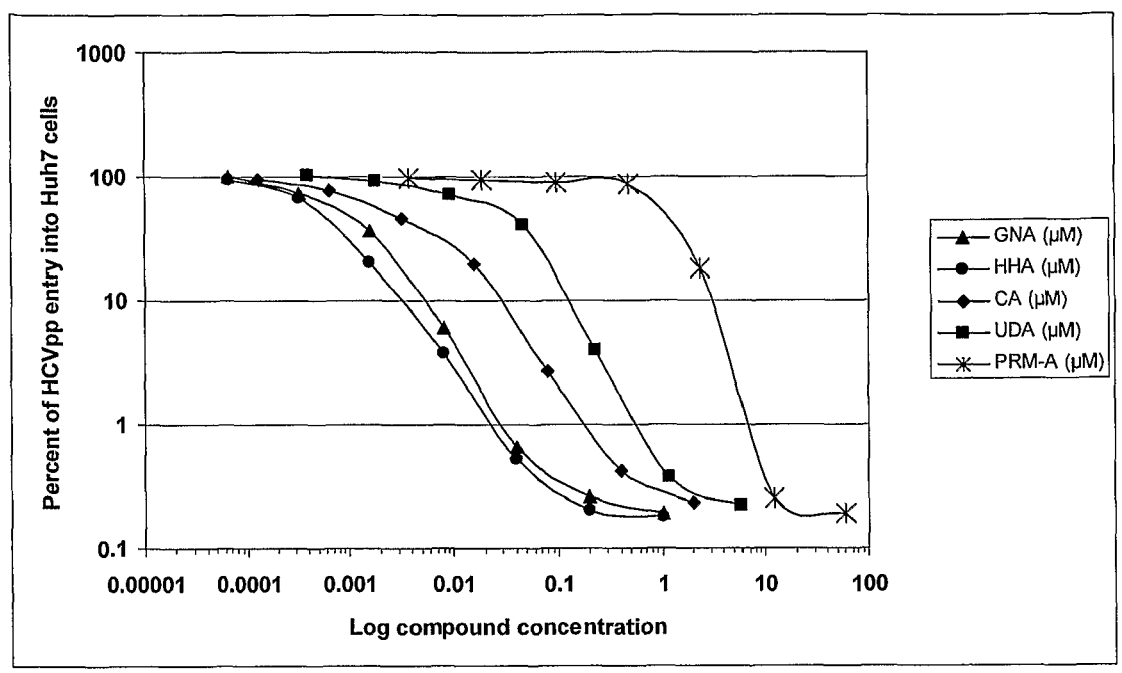

FIG. 5: inhibition of HCV entry with different CBAs.

Figure 6:
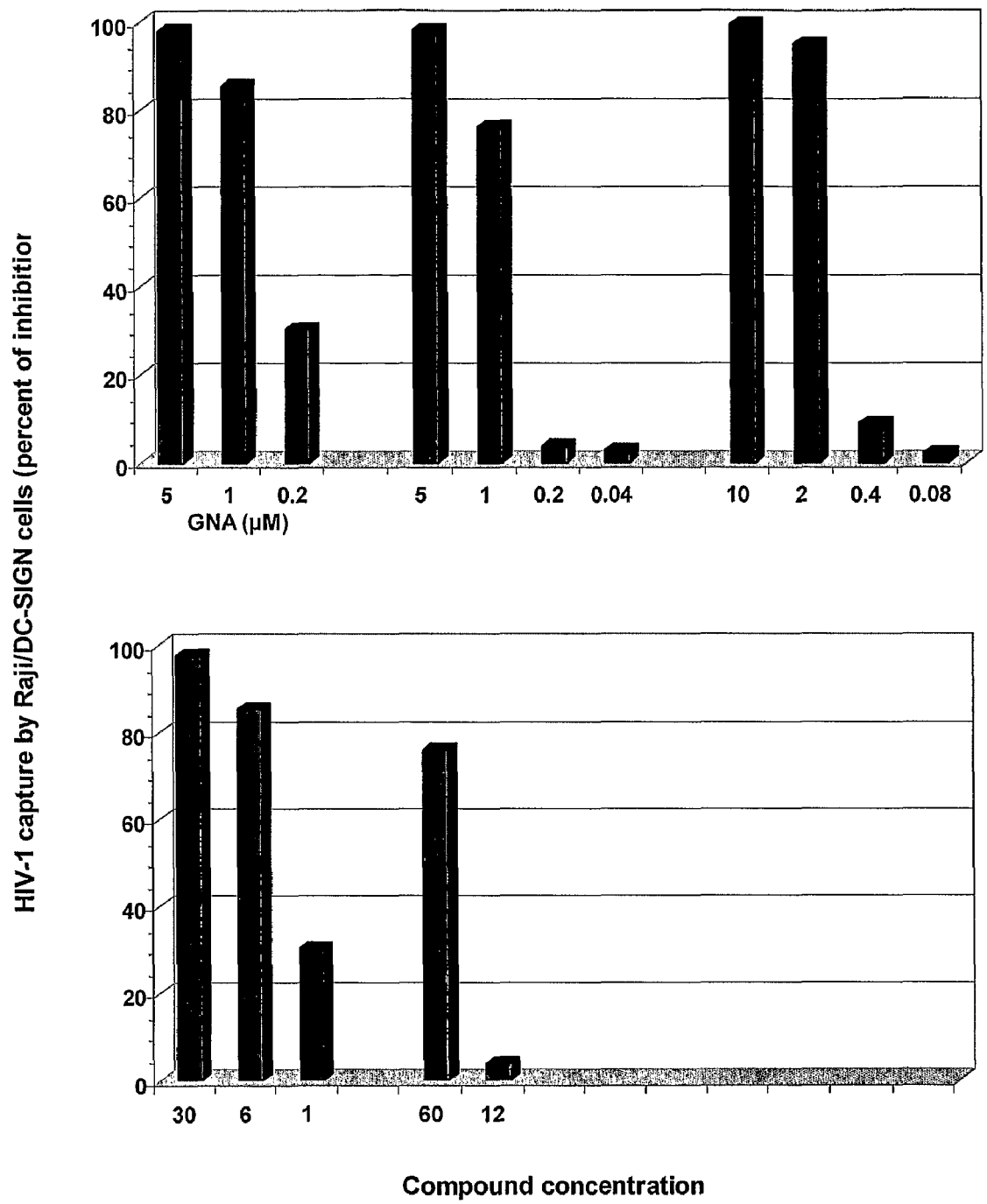

FIG. 6: HIV-1 capture by Raji/DC-SIGN cells.

DETAILED DESCRIPTION OF THE INVENTION

Definitions

In each of the following definitions, the number of carbon atoms represents the maximum number of carbon atoms generally optimally present in the substituent or linker; it is understood that where otherwise indicated in the present application, the number of carbon atoms represents the optimal maximum number of carbon atoms for that particular substituent or linker. Thus, also lower amounts of carbon atoms can be present like 1, 2, 3, 4, 5, 6, 7, 8, 9, 10, 11, 12, 13, 14 or 16.

The term "$C_1$-$C_{16}$ hydrocarbon group" as used herein refers to $C_1$-$C_{16}$ normal, secondary, tertiary unsaturated or saturated, acyclic or cyclic, including aromatic hydrocarbons and combinations thereof. This term therefore comprises alkyl, alkenyl, alkynyl, cycloalkyl, cycloalkenyl, cycloalkynyl, aryl, arylalkyl, arylalkenyl, arylakynyl, among others. When referring to a "hydrocarbon group which optionally includes one or more heteroatoms, said heteroatoms being selected from the groups consisting of O, S, and N", this includes alkyl-O-alkyl, alkenyl-O-alkyl, arylalkoxy, benzoyl, heterocycles, heterocycle-alkyl, heterocycle-alkoxy, among others.

The term "alkyl" as used herein refers to $C_1$-$C_{16}$ normal, secondary, or tertiary hydrocarbon chains. Examples are methyl, ethyl, 1-propyl, 2-propyl, 1-butyl, 2-methyl-1-propyl (1-Bu), 2-butyl(s-Bu) 2-methyl-2-propyl(t-Bu), 1-pentyl(n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl and n-icosyl.

As used herein and unless otherwise stated, the term "cycloalkyl" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein and unless otherwise stated, the term "cycloalkylene" refers to a cyclic hydrocarbon radical of 3-10 carbon atoms, and having two monovalent radical centers derived by the removal of two hydrogen atoms from the same or two different carbon atoms of a parent alkane; i.e. the divalent hydrocarbon radical corresponding to the above defined $C_{3-10}$ cycloalkyl.

The terms "alkenyl" and "cycloalkenyl" as used herein is C2-C18 normal, secondary or tertiary and respectively C3-10 cyclic hydrocarbon with at least one site (usually 1 to 3, preferably 1) of unsaturation, i.e. a carbon-carbon, sp2 double bond. Examples include, but are not limited to: ethylene or vinyl (—CH=CH2), allyl (—CH2CH=CH2), cyclopentenyl (—C5H7), and 5-hexenyl (—CH2CH2CH2CH=CH2). The double bond may be in the cis or trans configuration.

The terms "alkynyl" and "cycloalkynyl" as used herein refer respectively C2-C18 normal, secondary, tertiary or the C3-10 cyclic hydrocarbon with at least one site (usually 1 to 3, preferably 1) of unsaturation, i.e. a carbon-carbon, sp triple bond. Examples include, but are not limited to: acetylenic (—C≡CH) and propargyl (—CH2—C≡CH).

The term "aryl" as used herein means a aromatic hydrocarbon radical of 6-20 carbon atoms derived by the removal of hydrogen from a carbon atom of a parent aromatic ring system. Typical aryl groups include, but are not limited to 1 ring, or 2 or 3 or 4 rings fused together, radicals derived from benzene, naphthalene, spiro, anthracene, biphenyl, and the like.

"Arylalkyl" as used herein refers to an alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

The term "heterocyclic ring" or "heterocycle" as used herein means pyridyl, dihydroypyridyl, tetrahydropyridyl(piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include I-aziridyl, 1-azetedyl, 1-pyrrolyl, 1-imidazolyl, 1-pyrazolyl, and 1-piperidinyl.

"Carbocycle" means a saturated, unsaturated or aromatic ring system having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. Carbocycle thus includes some aryl groups.

As used herein and unless otherwise stated, the term "halogen" means any atom selected from the group consisting of fluorine (F), chlorine (Cl), bromine (Br) and iodine (I).

The term "carbohydrate" or "Sugar" or "glycan" refers to any cyclic or acyclic carbohydrate or multiple carbohydrates coupled to each other. Examples of carbohydrates are glucosyl, mannosyl, ristosaminyl, N-acylglucosaminyl, N-acylglucuronyl, glucosaminyl, glucuronyl, 4-epi-vancosaminyl, 3-epi-vancosaminyl, vancosaminyl, actinosaminyl, acosaminyl, glucosyl-vancosaminyl, glucosyl-4-epi-vancosaminyl, glucosyl-3-epi-vancosaminyl, glucosyl-acosaminyl, glucosyl-ristosaminyl, glucosyl-actinosaminyl, glucosyl-rhamnosyl, glucosyl-olivosyl, glucosyl-mannosyl, glucosyl-4-oxovancosaminyl, glucosyl-ureido-4-oxovancosaminyl, glucosyl(rhamnosyl)-mannosyl-arabinosyl, glucosyl-2-O-Leu.

"Mannose binding agents" or "mannose binding small molecules" are defined as having a dissociation constant lower than 100 μM, more in particular lower than 10 μM, for binding to mannose as determined by using the experimental setup as described in Shenoy, S. R. et al. in *J. Pharmacol. Exp. Ther.* 297: 704-710, 2001. "Carbohydrate binding small molecules" or "carbohydrate binding agents" are defined as compounds having a dissociation constant lower than 100 μM, more in particular lower than 10 μM, for binding to carbohydrates determined in analogy with the experimental setup as described in Shenoy, S. R. et al. in *J. Pharmacol. Exp. Ther.* 297: 704-710, 2001 (which included by reference herein).

(Human) viral pathogens with an envelop ("enveloped viruses") include herpesviridae, flaviviridae, poxyiridae, hepadnaviridae, togaviridae, arenaviridae, coronaviridae, retroviridae, bunyaviridae, orthomyxoviridae, paramyxoviridae and rhabdoviridae.

Description

The present invention relates to compounds that bind to viral envelop carbohydrates and to their use in anti-viral therapy or in vaccination strategies. The invention also relates to a novel method of treatment or prevention of viral infections of a mammal.

The compounds of the present invention block the interaction of carbohydrates of the envelop of viruses with their (co)receptors by binding to these carbohydrates, like for example gp120 of HIV, making the HIV entry impossible. Moreover, it has now been found that resistance development of HIV against such compounds that target the glycans on the envelope gp120 would result in markedly enhanced neutralisation of HIV by the host immune system. In other words, compounds that are directed against the carbohydrates present in the HIV gp120 glycans will select for mutant virus strains that progressively gain deletions in the glycosylation sites of the envelope (i.e. gp120). Such mutant virus will uncover previously hidden epitopes of the envelop and becomes highly susceptible to a markedly increased immunologic neutralisation by the immune system. We believe this novel approach may become an entirely new therapeutic concept that beneficially makes use of the high mutation rate of HIV and allows drug therapy to act in concert with a triggered immune response to more efficiently suppress HIV. Moreover, this approach can also be applied for the treatment of chronic infections by other viruses that contain a glycosylated envelope (i.e. hepatitis B and C). In this way, envelop carbohydrate interacting compounds which induce a high rate of resistance may be therefore preferred over compounds which induce a lower amount of resistance.

Neutralisation of HIV by the Host Immune System—Combination with Glycan Binding Compounds There is a wealth of direct and indirect evidence that the glycan shield of HIV prevents the immune system from an efficient neutralising attack against the virus. Lee and collaborators (12) identified five N-glycosylation sites on gp120 that resulted, upon deletion, in compromised infectivity of the mutated virus. Schonning et al. (13) demonstrated that HIV-1 strains lacking the highly conserved N-linked glycan at position 306 within the V3 loop of HIV gp120 are highly sensitive to neutralisation. Molecular clones of HIV lacking this N-306 glycosylation site reacquired this glycosylation site under in vitro immune selection with Mabs directed against the V3 loop. Bolmstedt et al. (14) demonstrated that N-306 glycans in gp120 shields HIV-1 from neutralising antibodies. Importantly, Reitter et al. (15) could convincingly demonstrate that Rhesus monkeys infected with mutant SIV strains lacking dual combinations of two N-linked glycosylation sites in the external envelope protein of the virus showed markedly increased antibody binding to specific peptides from this env region and showed substantial neutralising activity. The results demonstrated that N-glycosylation in SIV env plays a role in limiting the neutralising antibody response to SIV and in shielding the virus from immune recognition (15). It also illustrates that deletion of as less as two glycosylation sites in the viral envelope is already sufficient to trigger such a neutralising antibody response. Also Chackerian et al. (16) and Cheng-Mayer et al. (17) found that specific N-linked glycosylation modifications in the envelope V1 domain of SIV or in a simian/human immunodeficiency virus hybrid (SHIV) variant in vivo evolve in the host and alter recognition by neutralising antibodies. Finally, Kang et al. (18) recently reported that modified HIV env proteins with reduced glycosylation in domains surrounding the CD4 binding site or variable loop glycan-deleted virus mutants expose important neutralising epitopes at much higher levels than wild-type virus and may provide a tool for novel vaccine immunogens.

It has now been found that by using envelop carbohydrate binding compounds, mutations occur through which the protective glycan shield is destroyed, allowing increased recognition by the host immune system. Neutralizing antibodies will therefore be produced against the virus particle.

Moreover, the proposed concept should not only be effective against HIV, but also against chronic infections of other viruses containing a glycosylated envelope such as hepatitis B and C that require long-term chemotherapy. The fact that a marked number of HIV-infected individuals are co-infected by hepatitis B and/or hepatitis C virus, one single CBA could be effective against these viruses at the same time.

Deletion of N-glycosylation sites in hiv gp120 by carbohydrate-binding agents (cba): A variety of entry inhibitors select for virus strains that contain mutations in gp120 (32). These mutations allow the virus to escape drug pressure in cell culture. The mutations that are induced by the entry inhibitors such as dextran sulfate and AMD3100 consistently appear in gp120. Interestingly, the mannose-binding plant proteins were able to fully suppress the replication of these mutant virus strains (33). Remarkably, virus strains that emerged in the presence of escalating carbohydrate-binding drug concentrations predominantly showed mutations at N-glycosylation sites in gp120 but not gp41 (33,34). The degree of resistance correlated well with the number of deletions of the N-glycosylation sites in HIV-1 gp120. Mabs for which the epitope is located in the area of amino acids N295, N332 and N392 of gp120 (i.e. 2G12) (35) loose antiviral activity once one or two of these N-sites were mutated (33, 34). At the highest drug concentrations, virus isolates contained up to 7 or 8 different amino acid mutations either at the N-glycosylation sites or at the S/T amino acid position in the NXS/T glycosylation motif. In FIG. 2, the putative glycosylation sites in HIV-1(III$_B$) gp120 are shown (balls). The red-coloured balls represent those N-glycosylation sites that are deleted upon exposure to the mannose-binding proteins HHA, GNA and cyanovirin (33,34). Interestingly, these drug-resistant virus strains keep full sensitivity to the antiviral efficacy of other entry inhibitors of HIV (33). In another recent study, it was shown that the protein cyanovirin selected—besides of 2 point mutations at glycosylation sites 302 and 418—for a deletion in the V4 area of gp120 in which at least three high-mannose glycans were located, affording a virus strain with substantial resistance to this compound (36). Thus, the carbohydrate-binding proteins represent a unique class of conceptually novel anti-HIV compounds that select for an unusually specific and selective drug resistance profile. They represent the very first molecules that predominantly select for deletions of glycosylation sites in HIV gp120. The mannose-binding GNA and HHA proved non-toxic against the proliferation of mammalian cells in cell culture, non-mitogenic (in contrast with PHA) and not antimetabolically active. Intravenous bolus injection of 50 to 100 mg/kg in adult mice did not result in any visible side effects (30). These observations indicate that certain carbohydrate-binding plant proteins obviously do not show significant toxicity, and thus, that targetting mannose residues present on HIV gp120 can become a rather safe approach to develop novel classes of non-toxic carbohydrate-binding antiviral compounds. In fact, gp120 of HIV-1 consists of ~24 potential N-glycosylation sites, 13 sites containing high complex mannose-type and 11 sites containing high-mannose or hybrid-type glycans. The occurrence of high mannose-type glycan-containing proteins are more common in prokaryotes and viruses such as HIV but rather rare in mammalian cells. This may be one of the major reasons why several mannose-specific agents show poor if any toxicity in mammalian (cell) models under experimental conditions where they can fully inhibit virus entry. These observations are also in line with the findings that the mannose-specific cyanovirin proved effective in preventing SIV transmission in macaques in the absence of toxic side effects (31).

The carbohydrate binding agents (cba) concept: We now have a powerful tool in hand to propose a novel therapeutic approach of hiv treatment that is entirely new and different from all the existing therapeutic modalities and whose concept is completely opposite to any of the currently existing chemotherapeutic treatments. Exposure of HIV to carbohydrate-binding agents (CBA) will put the virus to the dilemma of either (i) becoming eventually eliminated from its host by being kept suppressed by the CBA, or (ii) escaping CBA drug pressure by mutating (deleting) its glycosylation sites in gp120 thereby becoming prone to immune neutralisation and elimination by the immune system of the host (Scheme 1). Therefore, it is conceivable that the concerted action between drug treatment and immune surveillance may markedly compromise the viability and infectivity potential of the virus in the infected host. Whereas so-far major attempts are made to design and develop drugs that should show an as high as possible genetic barrier aimed to delay drug resistance development as much as possible, the proposed approach makes use of the viral variability and inherent error-prone virus replication to generate mutant virus strains that presumably show deletions of glycosylation sites in its gp120 envelope glycoprotein. In addition, the proposed CBA approach makes use of a thus far unique concerted action of drug chemotherapy on the one hand and triggering of the immune system on the other hand, combining, in fact, chemotherapy and "therapeutic self-vaccination" in the host by the administration of one single drug. Moreover, one can even consider vaccination with partially deglycosylated gp120 prior to, or at the start of, CBA therapy. Exposure of HIV to CBAs will hit the Achilles heel of the virus: hiding its highly immunogenic and antigenic epitopes on gp120 by keeping a dense glycan shield. Taking this life-saving strategy of the HIV defense away, the virus will become prone to a continuous neutralisation by the immune system. Moreover, since it is known that transmission of HIV predominantly occurs through binding of gp120 of HIV with the glycan (mannose)-binding DC-SIGN after which exposure of the virus to T-lymphocytes by DC-SIGN-expressing dendritic cells occurs, it is conceivable that the efficient binding of DC-SIGN with gp120-mutated HIV will become suboptimal. In addition, since glycosylation of the native envelope protein helps to correct folding of gp160 and correct conversion to gp120 and gp41, it is expected that an increasing amount of deleted glycosylation sites in the precursor gp160 molecule will affect both correct folding and appropriate generation of gp120 and gp41, resulting in a compromised virulence/infectivity of HIV. It should be kept in mind that α-1,3- and α-1,6-mannose residues are still invariably present in each of the complex-type glycans, and that CBAs targetting other sugar specificities than mannose (i.e. N-acetylglucosamine, sialic acid, galactose, fucose, . . . ) should also be considered as valuable tools to afford the CBA concept.

Evidence from in vivo studies that the CBA concept could be regarded as effective: There have been carried out at least two in vivo (monkey) studies supporting that the CBA concept may be realistic, viable and achievable. Igarashi et al. (38) demonstrated that Rhesus macaques receiving a continuous infusion of cell-free HIV-1 particles showed a considerably lower half-life of the virion and the virus became eventually undetectable in blood if the monkeys had high-titer HIV-1-specific neutralising antibodies compared with those animals that lacked virus-specific Nabs. Moreover, Reiter et al. (15) showed that monkeys exposed to SIV strains that contain 2 deleted glycosylation sites in their env showed production of high-titer neutralising antibodies as well as a dramatic drop of infectious virus titer in the plasma (compared with wild-type virus). Thus, both monkey studies provide strong evidence that administration of CBAs to virus-infected animals may afford a marked trigger of the immune reaction and drop in virus load.

Novelty and uniqueness of the cba-concept: the proposed concept differs from the existing treatment modalities by at least 7 important characteristics. (i) Whereas appearance of mutations should be avoided in the current therapeutic drug targets for HIV treatment (i.e. reverse transcriptase (RT), protease (PR) and gp41), they are highly desirable in the CBA (targetting gp120) approach. (ii) Whereas drug resistance development weakens or annihilates the efficacy of the existing drugs, appearance of resistant viruses would increasingly potentiate the (immuno)therapeutic action of CBAs. (iii) Whereas all existing anti-HIV drugs interact with their target protein in a stoichiometric manner (1 drug molecule binds to 1 target protein molecule), many CBAs act at the same time to their (gp120) target (20 to 29 glycans on one single gp120 molecule; many gp120 molecules on one single virus particle or virus-infected cell) resulting in a high genetic barrier of the CBAs. (iv) Whereas current highly active antiretroviral therapy (HAART) consists of a combination of 3 or more compounds to be administered at the highest possible dose, the CBAs may (perhaps preferentially) be given as monotherapy before HAART comes into the picture. (v) Whereas none of the existing anti-HIV drugs (perhaps with the exception of lamivudine) directly, or indirectly interact with the immune system to exert their antiviral potential, CBAs will, beside a direct purely antiviral effect, also likely result in a strong response of the immune system by a triggered production of Nabs. (vi) The generation of deletions of glycosylation sites in gp120 may not only trigger production of Nabs against previously hidden strong immunogenic epitopes of gp120, but will likely also delay the initial spread of virus upon transmission from DC-SIGN-containing dendritic cells to T-lymphocytes. It would, however, be expected that mutated HIV will revert by incorporating again the glycans in its gp120 envelope after being transmitted to another individual in the absence of CBA treatment in the newly-infected person. (vii) CBA treatment may result in attenuated virus strains with lower virulence (infectivity) due to a compromised folding and conversion of precursor gp160 to gp120 and gp41. Thus, CBA exposure will concomitantly have multiple effects on different aspects of virus infection.

Whereas carbohydrate-binding proteins may not be very convenient to be used as systemic therapeutic agents, low-molecular weight compounds binding to carbohydrates would be much more convenient to exploit the CBA concept. In fact, the antibiotic Pradimicin A and several of its derivatives such as benenomicin, originally found in the fermentation broad of *Actinomadura hibisca* (39,40), bind to D-mannosides. Moreover, Pradimicin A had not only been shown to be endowed with antifungal activity (41,42) but also to inhibit HIV infection of T-cells through the interaction with the high mannose-type oligosaccharides on the HIV gp120 (43). Therefore, we believe that Pradimycin A should be considered as a prototype compound among the CBAs that might be helpful to prove the concept in vivo.

The present invention relates to the vaccination strategy of administering partially or fully deglycosilated envelope proteins, more in particular gp120 to a mammal for the prevention or treatment of a viral infection, more in particular of HIV, combined sequentially or concomitantly with a CBA.

Neutralisation of Enveloped Viruses other than HIV

Since the mechanism of antiviral effect is based on the binding of the glycans on the envelop proteins the inhibitory effect of carbohydrate binding small molecules and agents against other enveloped viruses was investigated.

The present invention also demonstrates that carbohydrate binding agents or small molecules can have an antiviral effect against other enveloped viruses than HIV, such as against HCV, HSV-1, HSV-2, VSV, RSV or Parainfluenza-3 virus.

Novel Envelop-carbohydrate Binding Small Molecules or Non Pectidic Polymers with Anti-viral Activity The present invention furthermore provides for novel compounds with anti-viral activity through their carbohydrate binding properties. The compounds of the present invention all have the common feature that they are small molecules. "Small molecules" are referred to as agents having a Mw<1000 (or Mw<500 or Mw<3000 in particular embodiments) and they are not a protein or of peptidic structure and in a particular embodiment, do not carry a glycan moiety. More in particular, the present invention relates to the use of said "carbohydrate binding small molecules" for the manufacture of a medicament for the prevention or treatment of infections of mammals (in particular infections with enveloped viruses), specifically excluding lectins (also called agglutinins). The term "Carbohydrate binding agents" refers to all carbohydrate binding agents including small molecules, polymers, proteins or peptides, comprising glycan moeieties or not. In a particular embodiment the present invention relates to mannose binding small molecules as defined herein. The molecules of the invention include, but are not limited to agents that contain one or several H-donating (i.e. OH, NH, $NH_2$), and/or H-accepting (i.e. C=0, —N, —OH) and/or aliphatic and/or aromatic (i.e. modified phenyl, pyridine, pyrimidine, indole, pyrrole, porphyns, porphyrins, phthalocyanines, etc.) stacking entities.

The term "compound" is used to refer to carbohydrate binding small molecules and agents, depending on the specific circumstances.

The carbohydrate binding small molecules and agents of the invention comprise, but are not limited to:

(a) Porphyrins and Derivatives Thereof

The present invention relates to the use of carbohydrate binding small molecules comprising a porphin structure (hereinafter referred to as "porphyrins"), in a particular embodiment comprising (divalent) cations such as, but not limited to, $Zn^{++}$, $Cu^{++}$, $Fe^{++}$, $Co^{++}$, $Mg^{++}$, $Mn^{++}$. Porphyrins are defined as "any of a group of compounds containing the porphin structure of four pyrrole rings connected by methine bridges in a cyclic configuration, to which a variety of side chains are attached; usually metalled, e.g., with iron to form heme" in the Academic Press Dictionary of Science Technology.

In a particular embodiment, the present invention also relates to porphyrins, comprising as substituents halogen atoms or $C_{1-16}$ hydrocarbon groups, which optionally includes one or more heteroatoms, said heteroatoms being selected from the groups consisting of O, S, and N (thus comprising aliphatic and/or heterocyclic and/or aromatic ring substituents such as quinolyl, (di)hydroxynaphtyl(cis or trans), phenylurea succinic acid, methylpyridinium, methylthioguanidinium, etc. groups). These modifications comprise substitutions on any carbon (or nitrogen) atom of the external ring system or on the bridging carbon atoms. Detailed examples and descriptions are given in Mizutani et al. (J. Am. Chem. Soc. 1997, 119: 8991-9001) which is incorporated herein by reference.

Examples thereof are as following:

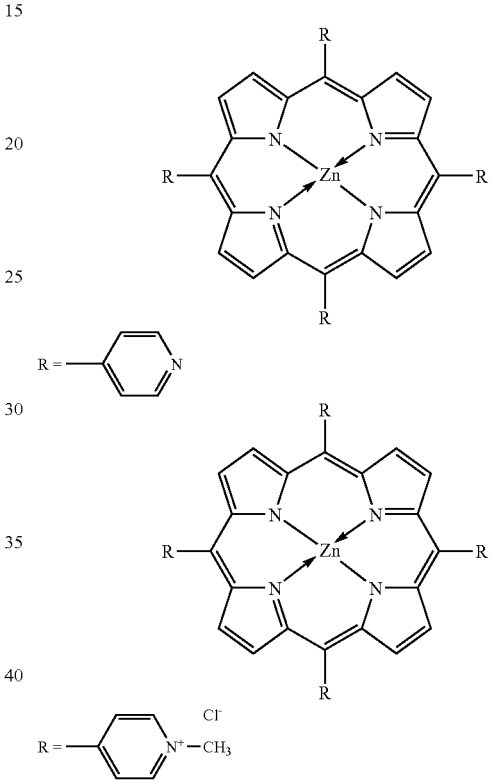

In yet another embodiment, the present invention relates to the use of the compounds comprising the structure of formula I,

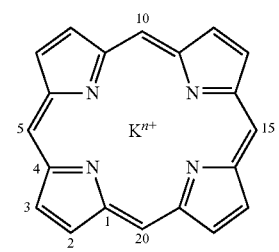

(I)

wherein
the porphin structure of formula I can be substituted at any position with halogen or $C_{1-16}$ hydrocarbon groups, which optionally includes one or more heteroatoms, said heteroatoms being selected from the groups consisting of O, S, and N. Specific examples of the substituents include quinolyl, (di)hydroxynaphtyl(cis or trans), phenylurea succinic acid, methylpyridinium and methylthioguanidinium groups); and in a particular embodiment, —the carbon atoms in the pentacyclic rings can be heteroatoms thereby creating heteroaromatic rings like imidazole, triazole, oxazole, etc.

A more particular embodiment of the present aspect relates to the use of compounds comprising formula I, and being substituted at position 5 and 10 or 5, 10, 15 and 20 with heterocyclic rings, more in particular with quinolyl rings or with heteroatom substituted aromatic rings, such as 2-hydroxynaphthyl or 2,7-dihydroxynaphthyl, which are positioned relatively to each other in the cis or trans configuration.

An embodiment of the present invention thus provides for the use of porphyrins (whether or not complexed to a (divalent) cation) or porphyrins according to formula I as described herein for the manufacture of a medicament for the prevention or treatment of viral infection with enveloped viruses in a mammal selected from Hepadnaviridae, like HBV (hepatitis B virus); the Coronaviridae, like SARS-CoV; the Herpesviridae; the Paramyxoviridae; the Orthomyxoviridae, like influenza virus A, B and C or the Flaviviridae such as HCV. In another particular embodiment, the present invention provides for methods of treatment of infections with envelop viruses selected from Hepadnaviridae, like HBV (hepatitis B virus); the Coronaviridae, like SARS-CoV; the Herpesviridae; the Paramyxoviridae; the Orthomyxoviridae, like influenza virus A, B and C or the Flaviviridae like HCV, comprising the use of porphyrins, in a particular embodiment according to formula I.

(b) Phthalocyanine Derivatives

The present invention also relates to the use of carbohydrate binding small molecules being phthalocyanine derivatives, in a particular embodiment comprising (divalent) cations such as, but not limited to, $Zn^{++}$, $Cu^{++}$, $Fe^{++}$, $Co^{++}$, $Mg^{++}$, $Mn^{++}$.

Phthalocyanines are compounds which comprise the structure of formula II,

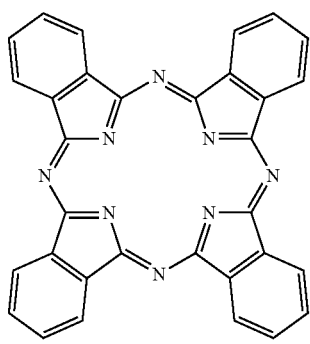

(II)

The present invention comprises phthalocyanine derivatives which comprise a structure according to formula II which is further substituted halogen atoms or $C_{1-16}$ hydrocarbon groups, which optionally includes one or more heteroatoms, said heteroatoms being selected from the groups consisting of O, S, and N. Specific examples of the substituents include quinolyl, (di)hydroxynaphtyl(cis or trans), phenylurea succinic acid, methylpyridinium and methylthioguanidinium groups).

A particular embodiment of the present invention relates to the use of Alcian Blue (formula IIa) or the carbohydrate small molecules according to formula IIa

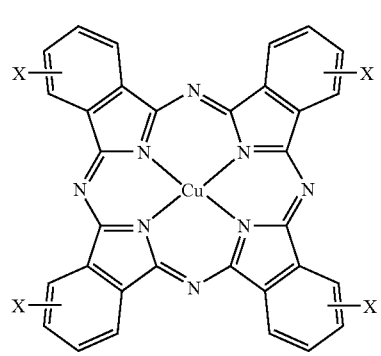

IIa wherein X is an onium group, such as a substituted or unsubstituted methylthioguanidinium group, such as

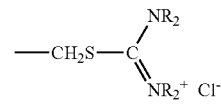

wherein R is selected from $C_{1-16}$ alkyl or aryl.

An embodiment of the present invention thus provides for the use of phthalocyanins (whether or not complexed to a (divalent) cation) or phthalocyanines according to formula II or IIa as described herein for the manufacture of a medicament for the prevention or treatment of a viral infection with enveloped viruses in a mammal. In a particular embodiment, the enveloped viruses for this embodiment are selected from Retroviridae, Hepadnaviridae, like HBV (hepatitis B virus); the Coronaviridae, like SARS-CoV; the Herpesviridae; the Paramyxoviridae; the Orthomyxoviridae, like influenza virus A, B and C or the Flaviviridae such as HCV. In another particular embodiment, the present invention provides for methods of treatment of infections with envelop viruses selected from Hepadnaviridae, like HBV (hepatitis B virus); the Coronaviridae, like SARS-CoV; the Herpesviridae; the Paramyxoviridae; the Orthomyxoviridae, like influenza virus A, B and C or the Flaviviridae like HCV, comprising the use of porphyrins, in a particular embodiment according to formula I.

(c) Phenylboronic Acid Comprising Compounds or Polymers

The compounds to be used in the present invention are for example such as described in Uchimura et al. (Biotechnol. Bioengineer. 2001, 72: 307-314) which is incorporated herein by reference. The carbohydrate binding small molecules or polymers of the present embodiment comprise the structure according to formula (III)

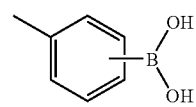

(III)

In a particular embodiment, a compound with 3-acrylamidophenylboronic acid containing N,N-dimethylacrylamide groups (poly AAPBA-DMAm) of formula IIIa can be used for the manufacture of a medicament for the prevention or treatment of viral infections in a mammal with an enveloped virus.

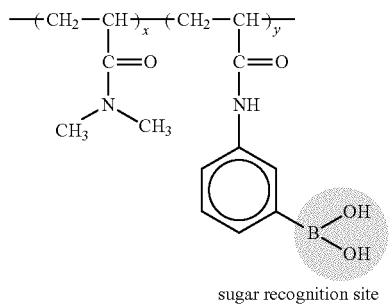

sugar recognition site

The present invention thus relates to the use compounds comprising phenylboronic acid, more in particular comprising 3-acrylamido-phenylboronic acid for the manufacture of a medicament for the prevention or treatment of viral diseases, more in particular viral infections with enveloped viruses, such as HIV-infections. Another embodiment relates to the use of 2,4-dimethyl-pentanedioic acid dimethylamide 3-boronic acid-phenyl-amide and polymerisation products thereof for the above purpose.

(d) Diethylenetriaminemetal(II) Complexes

The present invention relates to the use of compounds comprising diethylenetriaminemetal(II) complexes for the manufacture of a medicament for the prevention or treatment of viral diseases, more in particular viral infections with enveloped viruses, such as HIV-infections. In a particular embodiment the metal complex is a copper complex.

The present invention thus relates to the use of the compounds of formula IV

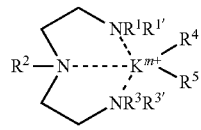

(IV)

wherein
  each $R^1$, $R^{1'}$ and $R^3$ are independently selected from hydrogen or alkyl,
  $R^2$ is selected from alkyl, alkene, alkyn, aryl, heterocyclic ring and each of alkyl, alkene, alkyn, aryl and heterocyclic ring unsubstituted or substituted with halogen, alkyl, alkene or alkyne;
  each $R^4$ and $R^5$ are selected from carboxyl, alkylcarboxyl, hydroxyl or amino or other functionalities with H-donor or H-acceptor capacities;
  $K^{m+}$ is selected from $Zn^{++}$, $Cu^{++}$, $Fe^{++}$, $Co^{++}$, $Mg^{++}$ or $Mn^{++}$.

Examples are compounds such as [(4-(N-vinylbenzyl)diethylenetriamine]copper(II) diformate [$Cu^{++}$(styDIEN)] (HCOO)$_2$] such as in Striegler (Tetrahedron 2001, 57: 2349-2354).

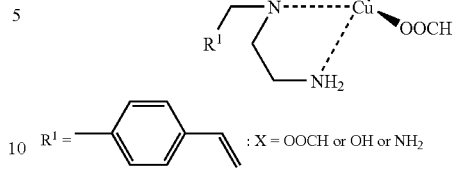

$R^1 =$ <image> : X = OOCH or OH or NH$_2$ (e) Acyclic Pyridine/Pyrimidine-based Carbohydrate Receptors:

The present invention relates to the use of compounds comprising the structure of formula Va or b,

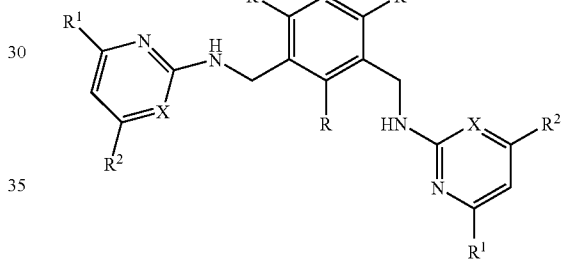

(Va)

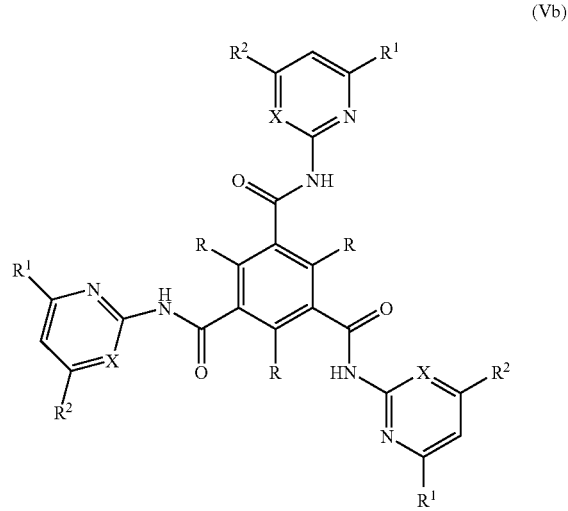

(Vb)

wherein
    each X is independently selected from $CR^3$ or N;
    each R, $R^1$ and $R^2$ are each independently selected from hydrogen, alkyl (such as methyl, ethyl, etc.) alkene, alkyne, hydroxy, amino or halogen;
    each $R^3$ is independently selected from hydrogen, alkyl (such as methyl, ethyl, etc.) alkene, alkyne;
for the manufacture of a medicament for the prevention or treatment of viral diseases, more in particular viral infections with enveloped viruses, such as HIV-infections.

In a particular embodiment, X is —CH—. In another particular embodiment, R, $R^1$ and $R^2$ are selected from methyl or ethyl.

Examples of such compounds are as in Mazik et al. (J. Am. Chem. Soc. 2005, 127: 9045-9052) which is incorporated herein by reference.

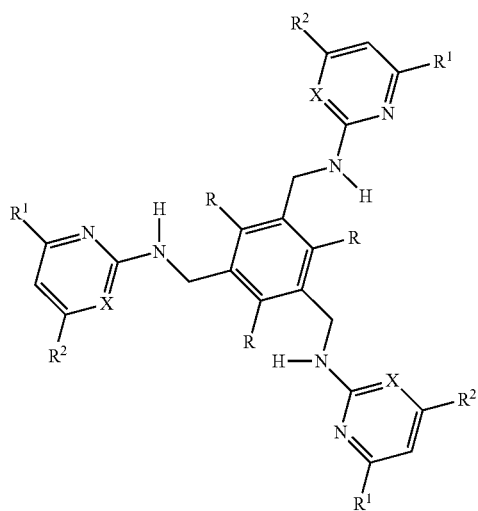

1: X = CH, R = $R^1$ = $R^2$ = $CH_3$
2: X = CH, R = $CH_2CH_3$, $R^1$ = $R^2$ = $CH_3$
3: X = N, R = $R^1$ = $R^2$ = $CH_3$ (f) Multivalent Polyphenolic Derivatives:

The present invention relates to the use of compounds comprising the structure of formula VI a, b or c

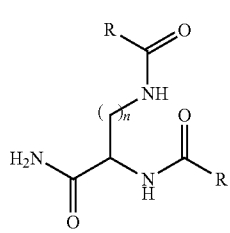

(VIa)

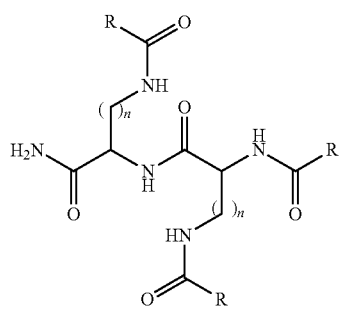

(VIb)

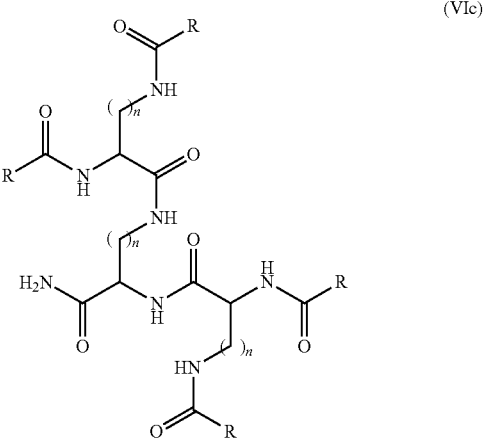

(VIc)

wherein each R is independently selected from 3,4,5-trihydroxy-1-phenyl, 3,5-hydroxyalkyl-4-hydroxy-1-phenyl, 2,6-dihydroxy-4-pyridinyl or 2,6-dihydroxyalkyl-4-pyridinyl;
    n is selected from 1, 2, 3 or 4;

for the manufacture of a medicament for the prevention or treatment of viral diseases, more in particular viral infections with enveloped viruses, such as HIV-infections.

As an example, the compounds can have a scaffold of diaminopropionic acid (preferably L, or D), diaminobutyric acid (preferably L, or D), ornithine (preferably L, or D), lysine (preferably D, or L) such as in Hamashin et al. (Bioorg. Med. Chem. 2003, 11: 4991-4997).

[Structure: 2 Copy — dihydroxybenzoyl-amide scaffold with galloyl groups]

2 Copy

[Structure: 4 Copy — tetra-galloyl scaffold]

4 Copy

| Scaffold amino acid | n | R = | #R groups |
|---|---|---|---|
| L-Diaminopropionic acid | 1 | Galloyl | 2 |
| L-Diaminobutyric acid | 2 | Galloyl | 2 |
| L-Ornithine | 3 | Galloyl | 2 |
| D-Lysine | 4 | Galloyl | 2 |
| L-Diaminopropionic acid | 1 | Galloyl | 4 |
| L-Diaminobutyric acid | 2 | Galloyl | 4 |
| L-Ornithine | 3 | Galloyl | 4 |
| D-Lysine | 4 | Galloyl | 4 |

As polyphenolic entities which can be used to create the compounds of this aspect of the invention, following mono-, di- or trihydroxybenzoyl molecules can be mentioned: gallic acid, tannic acid, epicatechin, epigallocatechin, myricetin, baicalein, quercetin, quercetagetin, ellagic acid, etc.

In a particular embodiment, the present invention relates to the use of the compounds specifically described in the articles Mizutani et al. (J. Am. Chem. Soc. 1997, 119: 8991-9001); Uchimura et al. (Biotechnol. Bioengineer. 2001, 72: 307-314); Striegler (Tetrahedron 2001, 57: 2349-2354); Mazik et al. (J. Am. Chem. Soc. 2005, 127: 9045-9052); Hamashin et al. (Bioorg. Med. Chem. 2003, 11: 4991-4997) which are all incorporated herein by reference.

(g) Pradimicin

The present invention relates to the use of pradimicin (S, A and other forms) and analogues thereof well known in the prior art, for the manufacture of a medicament for the prevention or treatment of viral diseases, more in particular viral infections with enveloped viruses, more in particular selected from Hepadnaviridae, like HBV (hepatitis B virus); the Coronaviridae, like SARS-CoV; the Herpesviridae; the Paramyxoviridae; or the Flaviviridae such as HCV.

In a particular embodiment, the present invention also relates to carbohydrate binding agents selected from the lectins or agglutinins which are well known in the art. More than a decade ago, plant lectins were reported to inhibit HIV replication in lymphocyte cell cultures through inhibition of virus/cell fusion. There exists a wide variety of specific sugar-recognizing lectins, from plants or animals, among which mannose-binding lectins are the most potent inhibitors of HIV replication in cell culture.

The present invention relates to the use of lectins and derivatives thereof, in particular mannose-specific and N-acetyl-glucosamine-specific lectins, for the prevention or treatment of enveloped virus infections other than Retroviridae and Orthomyxoviridae. In preferred embodiments said lectins are from *Galanthus nivalis* (GNA), *Hippeastrum hybrid* (HHA), *Narcissus pseudonarcissus* (NPA), *Cymbidium hybrid* (CA), *Epipactis helleborine* (EHA), *Listera Ovata* (LOA) and *Urtica dioica* (UDA).

The compounds of the invention are employed for the treatment or prophylaxis of viral infections, more in particular viral infections with enveloped viruses. When using one or more carbohydrate binding small molecules or polymers or agents as described herein:

the active ingredients of the compound(s) may be administered to the mammal (including a human) to be treated by any means well known in the art, i.e. orally, intranasally, subcutaneously, intramuscularly, intradermally, intravenously, intra-arterially, parenterally or by catheterization.

the therapeutically effective amount of the preparation of the compound(s), especially for the treatment of viral infections in humans and other mammals, preferably is a viral glycoprotein-binding amount. However, in order to obtain a mutation in the envelop, the dose used does not necessarily need to have a measurable inhibiting activity. Depending upon the pathologic condition to be treated and the patient's condition, the said effective amount may be divided into several sub-units per day or may be administered at more than one day intervals.

The present invention further relates to a method for preventing or treating a viral infection in a subject or patient by administering to the patient in need thereof a therapeutically effective amount of the carbohydrate binding compounds as described herein. In the further description of the invention herein, on many instances HIV will be used as prototype virus infection for the enveloped virus infections and where mentioned HIV for administration modes, combination therapies, compositions, etc, the same would count for other enveloped viruses.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon Cl<1, Cl=1, or Cl>1, respectively.

Synergistic activity of the pharmaceutical compositions or combined preparations of this invention against viral infection may also be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x + FIC_y$) is equal to 1.0, the combination is said to be additive; when it is between 1.0 and 0.5, the combination is defined as subsynergistic, and when it is lower than 0.5, the combination is defined as synergistic. When the minimum FIC index is between 1.0 and 2.0, the combination is defined as subantagonistic and, when it is higher than 2.0, the combination is defined as antagonistic.

This principle may be applied to a combination of different antiviral drugs of the invention or to a combination of the antiviral drugs of the invention with other drugs that exhibit anti-viral activity, more specifically for the virus of which the infection is sought to be treated or prevented.

The invention thus relates to a pharmaceutical composition or combined preparation having synergistic effects against a viral infection and containing:
Either:
A)
(a) a combination of two or more of the carbohydrate binding compounds described herein, and
(b) optionally one or more pharmaceutical excipients or pharmaceutically acceptable carriers, for simultaneous, separate or sequential use in the treatment or prevention of a viral infection or
B)
(c) one or more anti-viral agents, and
(d) at least one of the carbohydrate binding compounds described herein, and
(e) optionally one or more pharmaceutical excipients or pharmaceutically acceptable carriers, for simultaneous, separate or sequential use in the treatment or prevention of a viral infection.

Suitable anti-viral agents for inclusion into the synergistic antiviral compositions or combined preparations of this invention in particular for the treatment of HIV include practically all known anti-HIV compounds known at this moment such as nucleoside, nucleotide, and non-nucleoside reverse transcriptase inhibitors, protease inhibitors and integrase inhibitors, while for as an example HCV this could include interferon and/or ribavirin.

The pharmaceutical composition or combined preparation with synergistic activity against viral infection according to this invention may contain carbohydrate binding compounds described herein, over a broad content range depending on the contemplated use and the expected effect of the preparation. Generally, the content of the carbohydrate binding compounds described herein of the combined preparation is within the range of 0.1 to 99.9% by weight, preferably from 1 to 99% by weight, more preferably from 5 to 95% by weight.

According to a particular embodiment of the invention, the carbohydrate binding compounds described herein may be employed in combination with other therapeutic agents for the treatment or prophylaxis of viral infections. Specifically for HIV as an example, the invention therefore relates to the use of a composition comprising:
(a) one or more carbohydrate binding compounds described herein, and
(b) one or more HIV/protein-enzyme inhibitors as biologically active agents in respective proportions such as to provide a synergistic effect against a viral infection, particularly a HIV infection in a mammal, for instance in the form of a combined preparation for simultaneous, separate or sequential use in viral infection therapy of HIV.

When using a combined preparation of (a) and (b):
the active ingredients (a) and (b) may be administered to the mammal (including a human) to be treated by any means well known in the art, i.e. orally, intranasally, subcutaneously, intramuscularly, intradermally, intravenously, intra-arterially, parenterally or by catheterization.
the therapeutically effective amount of the combined preparation of (a) and (b), especially for the treatment of viral infections in humans and other mammals, particularly is a HIV replication or transmission inhibiting amount. More particularly, it is a HIV replication inhibiting amount of derivative (a) and a HIV enzyme inhibiting amount of inhibitor (b). Still more particularly when the said HIV enzyme inhibitor (b) is a reverse transcriptase inhibitor, its effective amount is a reverse transcriptase inhibiting amount. When the said HIV enzyme inhibitor (b) is a protease inhibitor, its effective amount is a protease inhibiting amount.
ingredients (a) and (b) may be administered simultaneously but it is also beneficial to administer them separately or sequentially, for instance within a relatively short period of time (e.g. within about 24 hours) in order to achieve their functional fusion in the body to be treated.

The invention also relates to the carbohydrate binding compounds described herein being used for inhibition of the replication of other viruses than HIV, particularly for the inhibition of other retroviruses and lentiviruses and also for the inhibition of the other enveloped viruses such as herpesviridae, flaviviridae, poxyiridae, hepadnaviridae, togaviridae, arenaviridae, coronaviridae, retroviridae, bunyaviridae, orthomyxoviridae, paramyxoviridae and rhabdoviridae.

The present invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

More generally, the invention relates to the carbohydrate binding small molecules described herein being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Those of skill in the art will also recognize that the carbohydrate binding compounds described herein may exist in many different protonation states, depending on, among other things, the pH of their environment. While the structural formulae provided herein depict the compounds in only one of several possible protonation states, it will be understood that these structures are illustrative only, and that the invention is not limited to any particular protonation state, any and all protonated forms of the compounds are intended to fall within the scope of the invention.

The term "pharmaceutically acceptable salts" as used herein means the therapeutically active non-toxic salt forms which the carbohydrate binding compounds described herein are able to form. Therefore, the compounds of this invention optionally comprise salts of the compounds herein, especially pharmaceutically acceptable non-toxic salts containing, for example, Na+, Li+, K+, Ca+2 and Mg+2. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions).

Metal salts typically are prepared by reacting the metal hydroxide with a compound of this invention. Examples of metal salts which are prepared in this way are salts containing Li+, Na+, and K+. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the carbohydrate binding compounds described herein as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and NX4+ (wherein X is C1-C4 alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as Na+ and NX4+ (wherein X typically is independently selected from H or a C1-C4 alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and sterochemical forms, which the carbohydrate binding compounds described herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the carbohydrate binding compounds described herein may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a carbohydrate binding compounds described herein can be separated substantially free of its opposing enantiomer by a method such as formation of diastereomers using optically active resolving agents ("Stereochemistry of Carbon Compounds," (1962) by E. L. Eliel, McGraw Hill; Lochmuller, C.

H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched compounds of the invention. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds according to the formulas of the application like (I) or (II) may easily be determined by those skilled in the art while using well-known methods such as, for example, X-ray diffraction or NMR.

The carbohydrate binding compounds described herein may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Carbohydrate binding compounds as described herein and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present invention comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat.

Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range of 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The carbohydrate binding compounds described herein can be used to provide controlled release of pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

EXAMPLES

The following examples are provided for the purpose of illustrating the present invention and should in no way be interpreted as limiting the scope thereof.

The compounds as described herein are tested in the assays as described hereunder.

Example 1

General methods for Antiviral Screening

Anti-H/V assay: The inhibitory activity of compounds of the invention were be tested for their potential to inhibit the replication of HIV and SIV in a cell culture model for acute infection. Compounds were tested against HIV-1 strains (HE, NL43, MN, III$_B$), HIV-2 strains (ROD, EHO, RF), and SIV (MAC251) for inhibition of virus-induced cytopathicity in MT-4 cells (or CEM or C8166 or Molt4/C8 cells), using the colorimetric test described by Pauwels et al. in *J. Virol. Methods* (1988) 20:309-321 or a microscopic investigation of the cytopathogenic effect, evaluation being made 4 to 5 days post-infection. For example microtiter 96-well plates containing ~3×10$^5$ CEM cells/ml, infected with 100 CCID$_{50}$ of HIV per ml and containing appropriate dilutions of the test compounds were used.

A rapid and automated assay procedure was used for the in vitro evaluation of anti-HIV agents. An HTLV-1 transformed T4-cell line MT-4, which was previously shown to be highly susceptible to and permissive for HIV infection, can serve as the target cell line. Inhibition of the HIV-induced cytopathogenic effect was used as the end point. The viability of both HIV- and mock-infected cells was also assessed spectrophotometrically via in situ reduction of 3(4,5-dimethylthiazol-2-yl)-2,5-diphenyltetrazolium bromide (MTT). Methods comprise for example the microscopic examination of CEM, C8166 or Molt4/C8 giant (syncytium) cell formation, after 4 to 5 days of incubation at 37° C. in a CO$_2$-controlled humidified atmosphere. The 50% cytotoxic concentration (CC$_{50}$ in μg/ml) is defined as the concentration of compound that reduces the absorbance of the mock-infected control sample by 50%. The percent protection achieved by the compound in HIV-infected cells is calculated by the following formula:

$$\frac{(OD_T)_{HIV} - (OD_C)_{HIV}}{(OD_C)_{MOCK} - (OD_C)_{HIV}} \text{ expressed in \%}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values are determined at 540 nm. The dose achieving 50% protection according to the above formula is defined as the 50% inhibitory concentration (IC$_{50}$ in μg/ml). The ratio of CC$_{50}$ to IC$_{50}$ is defined as the selectivity index (SI).

Cells: MT-4 cells (Miyoshi et al., 1982) were grown and maintained in RPMI 1640 medium supplemented with 10% heat-inactivated fetal calf serum, 2 mM L-glutamine, 0.1% sodium bicarbonate, and 20 μg of gentamicin per ml.

Viruses: The HIV-1 (IIIB) strain was obtained from the National Institutes of Health (Bethesda, Md.). The HIV-2 (ROD, EHO) (Barr-Sinoussi et al., 1983) stock is obtained from culture supernatant of HIV-2 infected cell lines. Mac251 is a SIV strain.

References

Barré-Sinoussi, F., Chemann, J. C., Rey, F., Nugeyre, M. T., Chamaret, S., Gruest, J., Dauguet, C., Axler-Blin, C., V, Zinet-Brun, F., Rouzioux, C., Rozenbaum, W., Montagnier, L. (1983).

Isolation of a T-lyphotropic retrovirus from patient at risk for AIDS, *Science* (Wash D.C.) 220, 868-871. Miyoshi, I., Taguchi, H., Kobonishi, I., Yoshimoto, S., Ohtsuki, Y., Shiraishi, Y., and Akagi, T. (1982) Type C virus-producing cell lines derived from adult T cell leukemia *Gann mongr*, 28, 219-228.

Cytostatic activity assays: All assays are performed in 96-well microtiter plates. To each well are added 5–7.5×10$^4$ cells and a given amount of the test compound. The cells are allowed to proliferate for 48 h (murine leukemia L1210) or 72 h (human lymphocyte CEM and Molt4/clone 8) at 37° C. in a humidified CO$_2$-controlled atmosphere. At the end of the incubation period, the cells can be counted in a Coulter counter. The IC$_{50}$ (50% inhibitory concentration) was defined as the concentration of the compound that reduced the number of cells by 50%.

Inhibition of HIV-1 capture by Raji/DC-SIGN cells. HIV-1 particles (2.2 μg p24/ml) were exposed to serial dilutions of the test compounds (400 μl) for 30 min. Then, the drug-exposed virus suspensions (500 μl) were mixed with Raji/DC-SIGN cell suspensions (500 μl; 10$^6$ cells) for 60 min at 37° C. after which the cells were thoroughly washed twice with 40 ml culture medium as described above. This procedure resulted in a final dilution of the initial compound concentrations by at least 160.000-fold. The Raji/DC-SIGN cell cultures were then analysed for HIV-1 p24 Ag content.

Anti-BVDV Assay:

Cells and viruses: Madin-Darby Bovine Kidney (MDBK) cells are maintained in Dulbecco's modified Eagle medium (DMEM) supplemented with BVDV-free 5% fetal calf serum (DMEM-FCS) at 37° C. in a humidified, 5% CO$_2$ atmosphere. BVDV-1 (strain PE515) is used to assess the antiviral activity in MDBK cells. Vero cells (ATCC CCL81) are maintained in MEM medium supplemented with 10% inactivated calf serum, 1% L-glutamine and 0.3% bicarbonate.

Anti-BVDV assay. Ninety-six-well cell culture plates are seeded with MDBK cells in DMEM-FCS so that cells reached 24 hr later confluency. Then medium is removed and serial 5-fold dilutions of the test compounds are added in a total volume of 100 ul, after which the virus inoculum (100 ul) is added to each well. The virus inoculum used results in a greater than 90% destruction of the cell monolayer after 5 days incubation at 37° C. Uninfected cells and cells receiving virus without compound are included in each assay plate. After 5 days, medium is removed and 90 μl of DMEM-FCS and 10 ul of MTS/PMS solution (Promega) is added to each well. Following a 2 hr incubation period at 37° C. the optical density of the wells is read at 498 nm in a microplate reader. The 50% effective concentration (EC$_{50}$) value is defined as the concentration of compound that protects 50% of the cell monolayer from virus-induced cytopathic effect.

Production of pseudoparticles (HCVpp) and cell culture infection. To produce HCVpp, 293T cells (1.2×10$^6$) were lipofected at a 1:2 ratio of a NLluc$^+$env$^-$ reporter vector and a vector expressing the HCV envelope glycoproteins as previously described (Bertaux and Dragic, 2006). HCV envelope glycoprotein-encoding sequences corresponding to subtypes 1b and 2b were PCR-amplified from patient sera starting from the last 60 amino acids in the Core to the end of glycoprotein E2. Supernatants were collected 48 hours post lipofection, filtered (0.45μ) and stored at −80° C. until further use. HCVpp were tested by infection of Huh7 cells (5×10$^4$) and measuring luciferase activity (relative light units, RLU) 48 hours post infection using the Luciferase assay system according to the manufacturer's instructions.

Huh7 cells (2×10$^4$) were plated and 24 hours later infected with supernatants containing infectious HCVcc pre-mixed with serial dilutions of lectins or polyanions. Mannan (2.5 mg/ml; Sigma) was added to some of the mixtures prior to Huh7 infection. After 24 hours post infection, the mixture of virus and test compounds was replaced by fresh medium, cells were brought at 37° C. and luciferase activity was measured in the cell lysates 24 hours later.

To measure inhibition of HCVpp (1a,1b,2b) entry into Huh7 cells by CBA and polyanions, an essentially similar procedure has been used as described above for infectious HCVcc (2a).

Anti-Hepatitis B Virus assay: The tetracycline-responsive cell lines HepAD38 can be used (Ladner et al., 1997). These are hepatoma cells that have been stably transfected with a cDNA copy of the pregenomic RNA of wild-type virus. Withdrawal of tetracycline from the culture medium results in the initiation of viral replication. Cells are cultured at 37° C. in a humidified 5% CO2/air atmosphere in seeding medium, DMEM/Ham's F12 (50/50) supplemented with 10% (v/v) heat-inactivated fetal calf serum, 100 IU/ml penicillin, 50 µg/ml streptomycin, 100 µg/ml kanamycin, 400 µg/ml G418, and 0.3 µg/ml tetracycline. When the assay is started, the cells are seeded in 48-well plates at a density of 5×105/well. After 2-3 days the cultures are induced for viral production by washing with prewarmed PBS and are fed with 200 µl assay medium (seeding medium without tetracycline and G418) with or without the antiviral compounds. Medium is changed after 3 days. The antiviral effect is quantified by measuring levels of viral DNA in culture supernatant at day 6 post-induction, by a real time quantitative PCR (Q-PCR). The Q-PCR is performed with 3 µl of culture supernatant in a reaction volume of 25 µl using the TaqMan Universal PCR Master Mix (Applied Biosystems, Branchburg, N.J.) with forward primer (5'-CCG TCT GTG CCT TCT CAT CTG-3' (SEQ ID NO:1); final concentration: 600 nM), reversed primer (5'-AGT CCA AGA GTY CTC TTA TRY AAG ACC TT-3' (SEQ ID NO:2); final concentration: 600 nM), and Taqman probe (6-FAM-CCG TGT GCA CTT CGC TTC ACC TCT GC-TAMRA (SEQ ID NO:3); final concentration 150 nM). The reaction is analyzed using a SDS 7000 (Applied Biosystems, Foster City, Calif.). A plasmid containing the full length insert of the HBV genome is used to prepare the standard curve. The amount of viral DNA produced in treated cultures is expressed as a percentage of the mock treated samples. The cytostatic effect of the various compounds is assessed employing the parent hepatoma cell line HepG2. The effect of the compounds on exponentially growing HepG2 cells is evaluated by means of the MTS method (Promega). Briefly, cells are seeded at a density of 300/well (96 well plate) and are allowed to proliferate for 3 days in the absence or presence of compounds after which time cell density is determined.

Ladner, S. K., Otto, M. J., Barker, C. S., Zaifert, K., Wang, G. H., Guo, J. T., Seeger, C., King, R. W. (1997).

Inducible expression of human hepatitis B virus (HBV) in stably transfected hepatoblastoma cells: a novel system for screening potential inhibitors of HBV replication. Antimicrob. Agents Chemother. 41:1715-1720.

The antiviral measurements other than HIV, HBV, BVDV and HCV were based on the inhibition of virus-induced cytopathicity which was scored microscopically when the cytopathic effect (CPE) had reached 100% in the control (untreated) virus-infected cell cultures. VSV, RSV, parainfluenzα-3, HSV-1 and HSV-2 were exposed to confluent human embryonic lung fibroblast (HEL), African green monkey kidney (Vero) or human cervix carcinoma (HeLa) cell cultures in 96-well microtiter plates at 100 $CCID_{50}$ (cell culture infective dose-50) in the presence of various dilutions of the test compounds. At day 3 post infection, the CPE was microscopically recorded in each cell culture. The performance of these experiments are well known in the prior art.

Example 2

Materials and General Preparation Methods of Carbohydrate Binding Small Molecules or Agents The compounds of the present invention can easily be prepared by a person skilled in the art while using a series of chemical reactions known to those skilled in the art and as described in the prior art such as for (a) porphyrins and derivatives or analogues thereof as described in Mizutani et al. (J. Am. Chem. Soc. 1997, 119: 8991-9001);

(b) phenylboronic acid comprising compounds or polymers, such as described in Uchimura et al. (Biotechnol. Bioengineer. 2001, 72: 307-314);

(c) Diethylenetriaminecopper(II) complexes, such as in Striegler (Tetrahedron 2001, 57: 2349-2354);

(d) Acyclic pyridine/pyrimidine-based carbohydrate receptors, such as in Mazik et al., (J. Am. Chem. Soc. 2005, 127: 9045-9052); and for (e) Multivalent polyphenolic derivatives, such as in Hamashin et al. (Bioorg. Med. Chem. 2003, 11: 4991-4997);

which are all incorporated herein by reference.

Also the preparation of lectines and pradimicin is well known in the art.

Example 3

Inhibition of HIV and HCV Infection by CBA

The inhibitory activities of carbohydrate binding small molecules and agents against infectious HIV-1 (strain $III_B$), HIV-2 (strain ROD) and HCVcc (subtype 2a) were evaluated in human T lymphocyte cells (CEM) and human hepatocellular carcinoma cells (Huh-7), respectively (Table 1). The mannose-specific plant lectins GNA, HHA and CA inhibited infection by both types of viruses at $EC_{50}$s that varied over an order of magnitude, between 0.003 and 0.030 µM. The GlcNAc-specific plant lectin UDA and the mannose-specific non-peptidic antibiotic pradimicin A (PRM-A) also markedly inhibited HIV and HCVcc infection, although UDA was ten-fold more potent than PRM-A. There was a strong correlation between the inhibitory activity of the different CBA against both viruses (r=0.934, FIG. 4, panel A) and the potency of each CBA against HIV and HCV was within the same order of magnitude (Table 1, FIG. 4). In other words, the more inhibitory a CBA was against HIV, the more inhibitory it was against HCV. The effect of mannan on the antiviral activity of the CBA was investigated. Whereas the inhibitory activity of the mannose-specific lectins and PRM-A against HIV-1 could be efficiently diminished in the presence of mannan, the antiviral activity of the GlcNAc-specific UDA could only be decreased by 3-fold (Table 3). A similar reversal of the antiviral activity of the CBA by mannan was also observed in the infectious HCVcc assays (Table 3).

TABLE 1

Antiviral activity of CBA in cell culture with lectins and Pradimicin

| | $EC_{50}^a$ (µM) | | |
|---|---|---|---|
| Compound | HIV-1($III_B$) (CEM) | HIV-2(ROD) (CEM) | HCV (2a) (Huh7) |
| GNA | 0.018 ± 0.0 | 0.011 ± 0.007 | 0.007 ± 0.003 |
| HHA | 0.006 ± 0.001 | 0.016 ± 0.0 | 0.003 ± 0.001 |
| CA | 0.030 ± 0.010 | 0.009 ± 0.004 | 0.012 ± 0.009 |

TABLE 1-continued

| UDA | 0.140 ± 0.040 | 0.391 ± 0.106 | 0.176 ± 0.029 |
| PRM-A | 3.36 ± 1.2 | 1.80 ± 0.0 | 3.61 ± 0.78 |

[a]50% effective concentration, or compound concentration required to inhibit virus-induced cytopathicity in HIV, HSV, VSV, RSV and para-influenza virus-infected cell cultures or luciferase activity in HCV-infected Huh7 cell cultures by 50%. Data are the mean of at least two to three independent experiments (±SD).

Anti-HIV and -HCV activity of
Alcian Blue (AB) in cell culture
$EC50^{a}$ (µg/ml)

| HIV-1 (NL4.3) (CEM) | HIV-1$^{Rb}$ (N44.3) (CEM) | HUT-78/HIV$^{c}$ + Sup T-1 | HCVpp (1a) |
|---|---|---|---|
| 5 ± 1 | >50 | 4.5 ± 1.5$^{c}$ | 30$^{d}$ |

[a]50% Effective concentration.
[b]AB-resistant virus strain, containing a glycan deletion at position 461 (N461P) and position 635 (N635K).
[c]Giant cell formation in a co-cultivation assay.
[d]At 50 µg/ml, >90% inhibition was observed.
The $CC_{50}$ (cytotoxic concentration at which 50% of the cells die) in CEM cells for Alcian Blue is bigger or equal to 100 µg/mL.

Example 4

Inhibition of HCV Pseudovirus Entry by CBA

In order to reveal whether CBA also act at the level of HCV entry, we evaluated their ability to inhibit entry of pseudoparticles comprising the HCV envelope glycoproteins E1 and E2 into Huh-7 cells. FIG. 3 shows that the CBA inhibit HCVpp (subtype 1a) infection of Huh-7 cells in a dose-dependent fashion. As observed for HCVcc, the mannose-specific CBA GNA, HHA and CA most potently inhibited HCVpp (1a) infection, followed by GlcNAc-specific UDA and finally the mannose-specific non-peptidic PRM-A (FIG. 5, Table 2). Also, a similar dose-dependent inhibition by CBA was observed when pseudotypes bearing the envelope glycoproteins of subtypes 1b and 2b were used (Table 2). In general, the inhibitory potential of the CBA was even more pronounced against the HCV pseudoparticles than against HCVcc. However, there was a close correlation between the $EC_{50}$ of HCVcc and the $EC_{50}$ of HCVpp 1a, HCVpp 1b and HCVpp 2b (r=0.990, 0.813 and 0.840, respectively) pointing to the relevance of the HCVpp assays compared with the infectious HCVcc assay (FIG. 4, panels B, C and D).

TABLE 2

Antiviral activity of CBA in cell culture using pseudotype virus particles as the infectious agent

| | $EC_{50}^{a}$ (µM) | | | |
|---|---|---|---|---|
| Compound | HCVpp (1a) (Huh7) | HCVpp (1b) (Huh7) | HCVpp (2b) (Huh7) | VSVpp (C8166) |
| GNA | 0.0009 ± 0.0002 | 0.001 ± 0.0003 | 0.0026 ± 0.0001 | >2 |
| HHA | 0.0006 ± 0.0002 | 0.0009 ± 0.0001 | 0.0011 ± 0.0004 | — |
| CA | 0.0026 ± 0.0007 | 0.012 ± 0.005 | 0.0156 ± 0.0068 | >4 |
| UDA | 0.032 ± 0.015 | 0.019 ± 0.022 | 0.050 ± 0.054 | >11 |
| PRM-A | 1.17 ± 0.31 | 1.67 ± 0.06 | 0.924 ± 0.156 | >60 |

[a]50% effective concentration, or compound concentration required to inhibit luciferase activity in HCVpp-infected Huh7 cell cultures or GFP-related fluorescence in VSVpp-infected C8166 cell cultures by 50%. Data are the mean (±SD) of at least two independent experiments.

TABLE 3

Effect of mannan on the antiviral activity of CBA

| | HIV-1 $EC_{50}^{a}$ (µM) | | HCV(2a) $EC_{50}^{a}$ (µM) | |
|---|---|---|---|---|
| Compound | As such | +Mannan (2.5 mg/ml) | As such | +Mannan (2.5 mg/ml) |
| HHA | 0.008 ± 0.005 | 0.50 ± 0.17 | 0.003 ± 0.001 | >>0.50 |
| GNA | 0.013 ± 0.003 | 0.54 ± 0.22 | 0.007 ± 0.003 | 0.147 ± 0.039 |
| CA | 0.030 ± 0.010 | — | 0.012 ± 0.009 | 0.047 ± 0.027 |
| UDA | 0.149 ± 0.040 | 0.459 ± 0.0 | 0.176 ± 0.029 | 0.560 ± 0.108 |
| PRM-A | 5.3 ± 0.78 | 40 ± 13 | 3.61 ± 0.78 | >>30 |

[a]50% effective concentration required to inhibit HIV-1-induced cytopathicity in CEM cell cultures or luciferase activity in HCV-infected Huh7 cell cultures by 50%.

Example 5

Prevention of Virus Capture by Raji/DC-SIGN Cells

Raji B-lymphocyte cells were modified to express DC-SIGN at their cell surface (Geijtenbeek et al., 2000; Wu et al., 2004). When Raji/DC-SIGN cells were exposed to cell-free HIV-1(III$_B$) particles, they were able to efficiently capture the virus particles as evidenced by retention of p24 antigen of HIV-1 on the Raji/DC-SIGN cells (~1200 pg p24). Wild-type Raji/0 cells do not retain HIV-1 p24 (below detection limit of the assay) (data not shown). When HIV-1 was shortly (30 min) exposed to different concentrations of CBA and polyanions prior to addition to Raji/DC-SIGN cells and subsequent removal of unbound virus by several washing/centrifugation steps, the CBA dose-dependently prevented virus capture by Raji/DC-SIGN cells (FIG. 6). The CBA could prevent >90% of HIV-1 capture at concentrations >2 µM for GNA, HHA and CA; >10 µM for UDA and >60 µM for PRM-A.

Example 6

Anti-Influenza Activity

TABLE 5

Anti-influenza virus activity of CBA in MDCK cell cultures

| | $EC_{50}^a$ (µg/ml) | | |
|---|---|---|---|
| | Influenza A | | |
| Compound | $H_3N_2$ | $H_1N_1$ | Influenza B |
| HHA | 0.09 | 0.86 | — |
| GNA | 0.77 | 2.9 | — |
| UDA | 0.99 | 4.1 | — |
| CA | 0.30 | 1.7 | 0.8 |
| PRM-A | 1.6 | 1.9 | 2.4 |
| Alcian Blue | >20 | >20 | >20 |

$^a$50% Effective concentration.

REFERENCES

1. Burton, D. R. (2002) Antibodies, viruses and vaccines. Nature Rev. Immunol. 2, 706-713.
2. Burton, D. R. (1997) A vaccine for HIV type 1: the antibody perspective. Proc. Natl. Acad. Sci. USA 94, 10018-10023.
3. Wei, X., Decker, J. M., Wang, S., Hui, H., Kappes, J. C., Wu, X., Salazar-Gonzalez, J. F., Salazar, M. G., Kilby, J. M., Saag, M. S., Komarova, N. L., Nowak, M. A., Hahn, B. H, Kwong, P. D., and Shaw, G. M. (2003) Antibody neutralization and escape by HIV-1. Nature 422, 307-312.
4. Rudd, P. M., and Dwek, R. A. (1997) Glycosylation: heterogeneity and the 3D structure of proteins. Crit. Rev. Biochem. Mol. Biol. 32, 1-100.
5. Rudd, P. M., Elliott, T., Cresswell, P., Wilson, I. A., and Dwek, R. A. (2001) Glycosylation and the immune system. Science 291, 2370-2375.
6. Wilson, I. A., and Stanfield, R. L. (1995) A Trojan horse with a sweet tooth. Nature Struct. Biol. 2, 433-436.
7. Scanlan, C. N., Pantophiet, R., Wormald, M. R., Saphire, E. O., Stanfield, R., Wilson, I. A., Katinger, H., Dwek, R. A., Rudd, P. M., and Burton, D. R. (2002) The broadly neutralizing anti-human immunodeficiency virus type 1 antibody 2G12 recognizes a cluster of α1→2 mannose residues on the outer face of gp120. J. Virol. 76, 7306-7321.
8. Bertoletti, A., Sette, A., Chisari, F. V., Penna, A., Levrero, M., De Carli, M, Fiaccadori, F., and Ferrari, C. (1994) Natural variants of cytotoxic epitopes are T-cell receptor antagonists for antiviral cytotoxic T cells. Nature 369, 407-410.
9. Klenerman, P., Rowland-Jones, S., McAdam, S., Edwards, J., Daenke, S., Lalloo, D., Koppe, B., Rosenberg, W., Boyd, D., Edwrds, A., Giangrande, P., Rodney E., Phillips, R. E., and McMichael, A. J. (1994) Cytotoxic T-cell activity antagonized by naturally occurring HIV-1 Gag variants. Nature 369, 403-407.
10. Schwartz, O., Marechal, V., Le Gall, S., Lemonnier, F., and Heard, J. M. (1996) Endocytosis of major histocompatibility complex class I molecules is induced by the HIV-1 Nef protein. Nat. Med. 2, 338-342.
11. Ploegh, H. L. (1998) Viral strategies of immune evasion. Science 280, 248-253.
12. Lee, W.-R., Syu, W.-J., Du, B., Matsuda, M., Tan, S., Wolf, A., Essex, M., and Lee, T.H. (1992) Nonrandom distribution of gp120 N-linked glycosylation sites important for infectivity of human immunodeficiency virus type 1. Proc. Natl. Acad. Sci. USA 89, 2213-2217.
13. Schonning, K., Jansson, B., Olofsson, S., and Hansen, J.-E. S. (1996) Rapid selection for an N-linked oligosaccharide by monoclonal antibodies directed against the V3 loop of human immunodeficiency virus type 1. J. Gen. Virol. 77, 753-758.
14. Bolmstedt, A., Hinkula, J., Rowcliffe, E., Biller, M., Wahren, B., and Olofsson, S. (2001) Enhanced immunogenicity of a human immunodeficiency virus type 1 env DNA vaccine by manipulating N-glycosylation signals. Effects of elimination of the V3 306 glycan. Vaccine 20, 397-405.
15. Reiter, J. N., Means, R. E., and Desrosiers, R. C. (1998) A role for carbohydrates in immune evasion in AIDS. Nature Med. 4, 679-684.
16. Chackerian, B., Rundensey, L. M., and Overbaugh, J. (1997) Specific N-linked and O-linked glycosylation modifications in the envelope VI domain of simian immunodeficiency virus variants that evolve in the host alter recognition by neutralizing antibodies. J. Virol. 71, 7719-7727.
17. Cheng-Mayer, C., Brown, A., Harouse, J., Luciw, P. A., and Mayer, A. J. (1999) Selection for neutralization resistance of the simian human immunodeficiency virus sHIVSF33A variant in vivo by virtue of sequence changes in the extracellular envelope glycoprotein that modify N-linked glycosylation. J. Virol. 73, 5294-5300.
18. Kang, S. M., Quan, F. S., Huang, C., Guo, L., Ye, L., Yang, C., and Compans, R. W. (2005) Modified HIV envelope proteins with enhanced binding to neutralizing monoclonal antibodies. Virology 331, 20-32.
19. Helenius, A., and Aebi, M. (2001) Intracellular functions of N-linked glycans. Science 291, 2364-2369.
20. Leonard, C. K., Spellman, M. W., Riddle, L., Harris, R. J., Thomas, J. N., and Gregory, T. J. (1990) Assignment of intrachain disulfide bonds and characterization of potential glycosylation sites of the type 1 recombinant human immunodeficiency virus envelope glycoprotein (gp120) expressed in Chinese hamster ovary cells. J. Biol. Chem. 265, 10373-10382.
21. Balzarini, J., Schols, D., Neyts, J., Van Damme, E., Peumans, W. and De Clercq, E. (1991) α-(1-3)- and α-(1-6)-D-mannose-specific plant lectins are markedly inhibitory to human immunodeficiency virus and cytomegalovirus infections in vitro. Antimicrob. Agents Chemother. 35, 410-416.

22. Balzarini, J., Neyts, J., Schols, D., Hosoya, M., Van Damme, E., Peumans, W. and De Clercq, E. (1992) The mannose-specific plant lectins from *Cymbidium* hybrid and *Epipactis helleborine* and the (N-acetylglucosamine)$_n$-specific plant lectin from *Urtica dioica* are potent and selective inhibitors of human immunodeficiency virus and cytomegalovirus replication in vitro. *Antiviral Res.* 18, 191-207.
23. Van Damme, E. J. M., Peumans, W. J., Pusztai, A., and Barocz, S. (eds.) (1998) Handbook of Plant Lectins: Properties and Biomedical Applications. John Wiley & Sons, Chichester, N.Y.
24. Sharon, N., and Lis, H. (eds.) (2003) Lectins, 2$^{nd}$ ed., Kluwer Academic Publishers, Dordrecht, pp. 1-452.
25. Boyd, M. R., Gustafson, K. R., McMahon, J. B., Shoemaker, R. H., O'Keefe, B. R., Mori, T., Gulakowski, R. J., Wu, L., Rivera, M. I., Laurencot, C. M., Currens, M. J., Cardellina II, J. H., Buckheit Jr., R. W., Nara, P. L., Pannell, L. K., Sowder II, R. C., and Henderson, L. E. (1997) Discovery of cyanovirin-N, a novel human immunodeficiency virus-inactivating protein that binds viral surface envelope glycoprotein gp120: potential applications to microbicide development. *Antimicrob. Agents Chemother.* 41, 1521-1530.
26. Bolmstedt, A. J., O'Keefe, B. R, Shenoy, S. R., McMahon, J. B., and Boyd, M. R. (2001) Cyanovirin-N defines a new class of antiviral agent targeting N-linked, high-mannose glycans in an oligosaccharide-specific manner. *Mol. Pharmacol.* 59, 949-954.
27. Bokesch, H. R., O'Keefe, B. R., McKee, T. C., Pannell, L. K., Patterson, G. M., Gardella, R. S., Sowder 2nd, R. C., Turpin, J., Watson, K., Buckehti, R. W. Jr., and Boyd, M. R. (2003) A potent novel anti-HIV protein from the cultured cyanobacterium *Scytonema varium. Biochemistry* 42, 2578-2584.
28. Shibuya, N., Goldstein, I. J., Shafer, J. A., Peumans, W. J., and Broekaert, W. F. (1986) Carbohydrate binding properties of the stinging nettle (*Urtica dioica*) rhizome lectin. *Arch. Biochem. Biophys.* 249, 215-224.
29. Harata, K., and Muraki, M. (2000) Crystal structures of *Urtica dioica* agglutinin and its complex with tri-N-acetylchitotriose. *J. Mol. Biol.* 297, 673-681.
30. Balzarini, J., Hatse, S., Vermeire, K., Princen, K., Aquaro, S., Perno, C.-F., De Clercq, E., Egberink, H., Vanden Mooter, G., Peumans, W., Vandamme, E. and Schols, D. (2004) Mannose-specific plant lectins from the Amaryllidaceae family qualify as efficient microbicides for prevention of human immunodeficiency virus infection. *Antimicrob. Agents Chemother.* 48, 3858-3870.
31. Tsai, C.-C, Emau, P., Jiang, Y., Tian, B., Morton, W. R., Gustafson, K. R., and Boyd, M. R. (2003) Cyanovirin-N gel as a topical microbicide prevents rectal transmission of SHIV89.6P in macaques. *AIDS Res. Human Retrovir.* 19, 535-541.
32. Este, J. A. (2001) HIV resistance to entry inhibitors. *AIDS Rev.* 3, 121-132.
33. Balzarini, J., Van Laethem, K., Hatse, S., Vermeire, K., De Clercq, E., Peumans, W., Van Damme, E., Vandamme, A.-M., Bolmstedt, A. and Schols, D. (2004b) Profile of resistance of human immunodeficiency virus to mannose-specific plant lectins. *J. Virol.* 78, 10617-10627.
34. Balzarini, J., Van Laethem, K., Hatse, S., Froeyen, M., Van Damme, E., Peumans, W., De Clercq, E. and Schols, D. (2005) Marked depletion of glycosylation sites in HIV-1 gp120 under drug pressure by the mannose-specific plant lectins of *Hippeastrum hybrid* and *Galanthus nivalis. Mol. Pharmacol.,* 67, 1556-1565.
35. Calarese, D. A., Scanlan, C. N., Zwick, M. B., Deechongkit, S., Mimura, Y., Kunert, R., Zhu, P., Wormald, M. R., Stanfield, R. L., Roux, K. H., Kelly, J. W., Rudd, P. M., Dwek, R. A., Katinger, H., Burton, D. R., and Wilson, I. A. (2003) Antibody domain exchange is an immunological solution to carbohydrate cluster recognition. *Science* 300, 2065-2071.
36. Witvrouw, M., Fikkert, V., Hantson, A., Pannecouque, C., O'Keefe, B. R., McMahon, J., Stamatatos, L., De Clercq, E., and Bolmstedt, A. (2005) Resistance of human immunodeficiency virus type I to the high-mannose binding agents Cyanovirin N and Concanavalin A. *J. Virol.* 79, 7777-7784.
37. Kwong, P. D., Wyatt, R., Robinson, J., Sweet, R. W., Sodroski, J., and Hendrickson, W. A. (1998) Structure of an HIV gp120 envelope glycoprotein in complex with the CD4 receptor and a neutralizing human antibody. *Nature* 393, 648-659.
38. Igarashi, T., Brown, C., Azadegan, A., Haigwood, N., Dimitrov, D., Martin, M. A., and Shibata, R. (1999) Human immunodeficiency virus type 1 neutralizing antibodies accelerate clearance of cell-free virions from blood plasma. *Nature Med.* 5, 211-216.
39. Oki, T., Konishi, M., Tomatsu, K., Tomita, K., Saitoh, K., Tsunakawa, M., Nishio, M., Miyaki, T., and Kawaguchi, H. (1988) Pradimicin, a novel class of potent antifungal antibiotics. *J. Antibiot.* 41, 1701-1704.
40. Gomi, S., Sezaki, M., Kondo, S., Hara, T., Naganawa, H., and Takeuchi, T. (1988) The structures of new antifungal antibiotics, benenomicin A and B. *J. Antibiot.* 41, 1019-1028.
41. Oki, T., Tenmyo, O., Hirano, M., Tomatsu, K., and Kamei, H. (1990) Pradimicins A, B and C: new antifungal antibiotics. II. In vitro and in vivo biological activities. *J. Antibiot.* 43, 763-770.
42. Kakushima, M., Masuyoshi, S., Hirano, M., Shinoda, M., Ohta, A., Kamei, H., and Oki, T. (1991) In vitro and in vivo antifungal activities of BMY-28864, a water-soluble pradimicin derivative. *Antimicrob. Agents Chemother.* 35, 2185-2190.
43. Tanabe-Tochikura, A., Tochikura, T., Yoshida, O., Oki, T., and Yamamoto, N. (1990) Pradimicin A inhibition of human immunodeficiency virus: attenuation by mannan. *Virology* 176, 467-473.

The invention claimed is:

1. A method for the treatment of a viral infection in a mammal infected with a virus selected from the group consisting of human immunodeficiency virus 1 (HIV-1), human immunodeficiency virus 2 (HIV-2), hepatitis C virus (HCV), influenza A, and influenza B, said method comprising administering to the mammal in need of such treatment a therapeutically effective amount of a carbohydrate-binding molecule as an active ingredient, wherein said carbohydrate-binding molecule is a phenylboronic acid-comprising polymer comprising the structure according to formula (III)

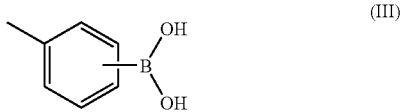

(III)

in a mixture with at least a pharmaceutically acceptable carrier.

2. A method for the treatment of a viral infection in a mammal infected with a virus, wherein said virus is selected from the group consisting of human immunodeficiency virus 1 (HIV-1), human immunodeficiency virus 2 (HIV-2), hepatitis C virus (HCV), influenza A, and influenza B, said method comprising administering to the mammal in need of such treatment a therapeutically effective amount of a phenylboronic acid-comprising polymer comprising the structure according to formula (III)

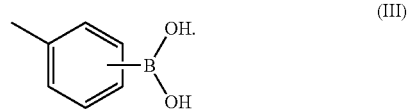

(III)

3. The method according to claim 1, wherein said phenylboronic acid-comprising polymer is a 3-acrylamidophenylboronic acid-comprising polymer.

4. The method according to claim 2, wherein said phenylboronic acid-comprising polymer is a 3-acrylamidophenylboronic acid-comprising polymer.

5. The method according to claim 1, wherein said phenylboronic acid-comprising polymer is a copolymer of 3-acrylamidophenylboronic acid with N,N-dimethylacrylamide.

6. The method according to claim 2, wherein said phenylboronic acid-comprising polymer is a copolymer of 3-acrylamidophenylboronic acid with N,N-dimethylacrylamide.

* * * * *